(12) United States Patent
Weisbart

(10) Patent No.: US 10,702,543 B2
(45) Date of Patent: Jul. 7, 2020

(54) INTRANUCLEAR PROTEIN TRANSDUCTION THROUGH A NUCLEOSIDE SALVAGE PATHWAY

(71) Applicant: The United States Government as represented by The Department of Veterans Affairs, Washington, DC (US)

(72) Inventor: Richard H. Weisbart, Los Angeles, CA (US)

(73) Assignee: The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/617,494

(22) Filed: Feb. 9, 2015

(65) Prior Publication Data

US 2015/0366986 A1    Dec. 24, 2015

Related U.S. Application Data

(63) Continuation of application No. 12/126,810, filed on May 23, 2008, now Pat. No. 8,956,825.

(60) Provisional application No. 60/931,855, filed on May 24, 2007.

(51) Int. Cl.
| | |
|---|---|
| *A61K 47/68* | (2017.01) |
| *C12N 15/63* | (2006.01) |
| *C12N 15/11* | (2006.01) |
| *C07K 16/44* | (2006.01) |
| *A61K 31/713* | (2006.01) |
| *G01N 33/50* | (2006.01) |
| *C12N 15/113* | (2010.01) |
| *A61K 38/00* | (2006.01) |

(52) U.S. Cl.
CPC ........ *A61K 31/713* (2013.01); *A61K 47/6843* (2017.08); *C07K 16/44* (2013.01); *C12N 15/113* (2013.01); *G01N 33/5035* (2013.01); *A61K 38/00* (2013.01); *C07K 2317/622* (2013.01); *C07K 2317/77* (2013.01); *C07K 2317/82* (2013.01); *C12N 2310/14* (2013.01); *C12N 2310/3513* (2013.01); *C12N 2320/30* (2013.01)

(58) Field of Classification Search
CPC  A61K 47/6843; A61K 47/6811; A61K 38/00; A61K 31/713; C07K 16/44; C07K 2317/77; C07K 2317/82; C07K 2317/622; G01N 33/5035; G01N 33/5082; C12N 15/63; C12N 15/11; C12N 2320/30; C12N 2310/3513
See application file for complete search history.

(56) References Cited

U.S. PATENT DOCUMENTS

| | | | |
|---|---|---|---|
| 4,812,397 | A  | 3/1989  | Weisbart |
| 6,130,065 | A  | 10/2000 | Belt et al. |
| 6,232,444 | B1 | 5/2001  | Weisbart |
| 7,189,396 | B1 | 3/2007  | Weisbart |
| 7,381,799 | B2 | 6/2008  | Papathanassiu |
| 2005/0074771 | A1 | 4/2005 | Cook |
| 2006/0003362 | A1 | 1/2006 | Zerangue |

FOREIGN PATENT DOCUMENTS

| | | |
|---|---|---|
| WO | WO 1997/32602    | 9/1997 |
| WO | WO 1998/016247 A1 | 4/1998 |
| WO | WO 1998/29437 A2  | 7/1998 |
| WO | WO 20051117562 A2 | 12/2005 |

OTHER PUBLICATIONS

Skolnick et al., Trends in Biotechnology, vol. 18, pp. 34-39, 2000.*
Lloyd et al., Protein Engineering, Design & Selection 22:159-168 (Year: 2009).*
Edwards et al., J Mol Biol. 334(1): 103-118 (Year: 2003).*
Chen et al., EMBO J., 14: 2784-2794 (Year: 1995).*
Hansen et al., "Intranuclear protein transduction through a nucleoside salvage pathway", *J. Biol. Chem.*, 282(29):20790-3 (2007).
Nagai et al.: "*Mouse equilibrative nucleoside transporter 2 (mENT2) transports nucleosides and purine nucleobases differing from human and rat ENT2*"; Biol. Pharm. Bull., 2007, 30(5): 979-981.
Zhang et al.: "*The role of nucleoside, transporters in cancer chemotherapy with nucleoside drugs*", Cancer Metastasis Rev., 2007, 26(1):85-110.
European Search Report from EP 08 76 9716, dated Oct. 31, 2011.
Kong et al.: "*Mammalian Nucleoside Transporters*", Current Drug Metabolism, 2004 vol. 5: 63-84.
Meas et al.: "*Polyreactive anti-DNA monoclonal antibodies and a derived peptide as vectors for the intracytoplasmic and intranuclear translocation of macromolecules*", 1998, Proc. Natl. Acad. Sci., 95:5601-5606.

(Continued)

Primary Examiner — Phuong Huynh
(74) *Attorney, Agent, or Firm* — DLA Piper LLP (US)

(57) ABSTRACT

Provided herein are conjugate molecules containing a substrate for a nucleoside transport pathway linked to an active agent, wherein the conjugate can be transported into a cell or into the nucleus of a cell via a cellular nucleoside transport pathway. Further provided are methods of delivering a conjugate molecule to a target cell expressing a nucleoside transport pathway, wherein the conjugate contains a substrate for the nucleoside transport pathway linked to an active agent. Also provided are methods for screening for conjugates that are transported by nucleoside transport pathways. Further provided are methods of treating a patient having a disease or disorder affecting tissues expressing nucleoside transport pathways, in which a conjugate containing an agent effective in treating the disorder is administered to the patient. Also provided are methods of treating a patient having an autoimmune disorder involving administering to the patient a compound that inhibits a nucleoside transport pathway.

5 Claims, 4 Drawing Sheets

Specification includes a Sequence Listing.

(56) References Cited

OTHER PUBLICATIONS

De Coupade et al.: "*Novel human-derived cell-penetrating peptides for specific subcellular delivery of therapeutic biomolecuies*"; Biochem. 1, 2005, 390:407-418.

Mackey et al.: "*Gemcitabine Transport in Xenopus Oocytes Expressing Recombinant Plasma Membrane Mammalian Nucleoside Transporters*", Journal of the National Cancer Institute, 1999, 91(21):1876-1881.

Beal, Paul R. et al.: "*The equilibrative nucleoside transporter family, SLC29*"; Pflugers Arch: Eur J Physiol, vol. 447, No. 5, Feb. 1, 2004, pp. 735-743, XP055317198.

European Examination report dated Nov. 14, 2016, regarding EP 08 769 716.5.

Hansen et al.: "*Antibody mediated transduction of therapeutic proteins into living cells*"; Scientific World J., vol. 5, No. 9, Sep. 16, 2005, pp. 782-788, XP008110943.

Weisbart, R. H. et al: "*An intracellular delivery vehicle for protein transduction of micro-dystrophin*"; J Drug Targeting, vol. 13, No. 2, Feb. 1, 2005, pp. 81-87.

Weisbart, R. H. et al: "*An Autoantibody is Modified for Use as a Delivery System to Target the Cell Nucleus: Therapeutic Implications*"; JAI, vol. 11, No. 5, Oct. 1, 1998, pp. 539-546, XP027373229.

Hansen, J.E. et al.: "Antibody-Mediated p53 Protein Therapy Prevents Liver Metastasis In vivo", Cancer Res, Feb. 15, 2007, 67(4), pp. 1769-1774.

Weidle, U.H. et al.: "*The Translational Potential for Target Validation and Therapy Using Intracellular Antibodies in Oncology*", Cancer Genomics & Proteomics, 2013, vol. 10, pp. 239-250.

Weisbart, R.H. et al.: "*Novel Protein Transfection of Primary Rat Cortical Neurons Using an Antibody That Penetrates Living Cells*", J. Immunology, 2000, vol. 164, pp. 6020-6026.

Canadian Office Action dated Nov. 17, 2015, regarding CA 2,688,240.

Canadian Office Action dated Nov. 20, 2017, regarding CA 2,688,240.

Zack, D.J., et al.: "Mechanisms of cellular penetration and nuclear localization of an anti-double strand DNA autoantibody."; J Immunol., 157(5), pp. 2082-2088, Sep. 1, 1996. (Abstract).

European Search Report dated Mar. 25, 2019, regarding EP 18 19 2326.

Fukuda et al.: "Autophagy and Mistargeting of Therapeutic Enzyme in Skeletal Muscle in Pompe Disease"; Molecular Therapy, Dec. 2006, vol. 14, No. 6, pp. 831-839.

Ward, Jeffrey L. et al.: "Kinetic and Pharmacological Properties of Cloned Human Equilibrative Nucleoside Transporters, ENT1 and ENT2, Stably Expressed in Nucleoside Transporter-deficient PK15 Cells : ENT2 exhibits a low affinity for guanosine, and cytidine but a high affinity for inosine"; J. Bio Chemistry, Mar. 24, 2000, vol. 275, No. 12, pp. 8375-8381.

\* cited by examiner

```
   1 gggctgcgct gtccagctgt ggctatggcc ccagccccga gatgaggagg gagagaacta
  61 ggggcccgca ggcctgggaa tttccgtccc ccaccaagtc cggatgctca ctccaaagtc
 121 tcagcaggcc cctgagggag ggagctgtca gccagggaaa accgagaaca ccatcaccat
 181 gacaaccagt caccagcctc aggacagata caaagctgtc tggcttatct tcttcatgct
 241 gggtctggga acgctgctcc cgtggaattt tttcatgacg gccactcagt atttcacaaa
 301 ccgcctggac atgtcccaga atgtgtcctt ggtcactgct gaactgagca aggacgccca
 361 ggcgtcagcc gcccctgcag cacccttgcc tgagcggaac tctctcagtg ccatcttcaa
 421 caatgtcatg accctatgtg ccatgctgcc cctgctgtta ttcacctacc tcaactcctt
 481 cctgcatcag aggatccccc agtccgtacg gatcctgggc agcctggtgg ccatcctgct
 541 ggtgtttctg atcactgcca tcctggtgaa ggtgcagctg gatgctctgc ccttctttgt
 601 catcaccatg atcaagatcg tgctcattaa ttcatttggt gccatcctgc agggcagcct
 661 gtttggtctg gctggccttc tgcctgccag ctacacggcc cccatcatga gtggccaggg
 721 cctagcaggc ttctttgcct ccgtggccat gatctgcgct attgccagtg gctcggaact
 781 atcagaaagt gccttcggct actttatcac agcctgtgct gttatcattt tgaccatcat
 841 ctgttacctg ggcctgcccc gcctggaatt ctaccgctac taccagcagc tcaagcttga
 901 aggacccggg gagcaggaga ccaagttgga cctcattagc aaaggagagg agccaagagc
 961 aggcaaagag gaatctggag tttcagtctc caactctcag cccaccaatg aaagccactc
1021 tatcaaagcc atcctgaaaa atatctcagt cctggctttc tctgtctgct tcatcttcac
1081 tatcaccatt gggatgtttc agccgtgac tgttgaggtc aagtccagca tcgcaggcag
1141 cagcacctgg gaacgttact tcattcctgt gtcctgtttc ttgactttca atatctttga
1201 ctggttgggc cggagcctca cagctgtatt catgtggcct gggaaggaca gccgctggct
1261 gccaagcctg gtgctggccc ggctggtgtt tgtgccactg ctgctgctgt gcaacattaa
1321 gccccgccgc tacctgactg tggtcttcga gcacgatgcc tggttcatct tcttcatggc
1381 tgcctttgcc ttctccaacg gctacctcgc cagcctctgc atgtgcttcg ggcccaagaa
1441 agtgaagcca gctgaggcag agaccgcagg agccatcatg gccttcttcc tgtgtctggg
1501 tctggcactg ggggctgttt tctccttcct gttccgggca attgtgtgac aaaggatgga
1561 cagaaggact gcctgcctcc ctccctgtct gcctcctgcc ccttccttct gccagggtg
1621 atcctgagtg gtctggcggt ttttcttct aactgacttc tgctttccac ggcgtgtgct
1681 gggcccggat ctccaggccc tggggaggga gcctctggac ggacagtggg gacattgtgg
1741 gtttggggct cagagtcgag ggacggggtg tagcctcggc atttgcttga gtttctccac
1801 tcttggctct gactgatccc tgcttgtgca ggccagtgga ggctcttggg cttggagaac
1861 acgtgtgtct ctgtgtatgt gtctgtgtgt ctgcgtccgt gtctgtcaga ctgtctgcct
1921 gtcctggggt ggctaggagc tgggtctgac cgttgtatgg tttgacctga tatactccat
1981 tctccctgc gcctcctcct ctgtgttttt tccatgtccc cctcccaact ccccatgccc
2041 agtttttacc catcatgcac cctgtacagt tgccacgtta ctgccttttt taaaaatata
2101 tttgacagaa accaggtgcc ttcagaggct ctctgattta aataaacctt tcttgttttt
2161 tt
```

FIG. 1A

```
  1 mttshqpqdr ykavwliffm lglgtllpwn ffmtatqyft nrldmsqnvs lvtaelskda
 61 qasaapaapl pernslsaif nnvmtlcaml plllftylns flhqripqsv rilgslvail
121 lvflitailv kvqldalpff vitmikivli nsfgailqgs lfglagllpa sytapimsgq
181 glagffasva micaiasgse lsesafgyfi tacaviilti icylglprle fyryyqqlkl
241 egpgeqetkl dliskgeepr agkeesgvsv snsqptnesh sikailknis vlafsvcfif
301 titigmfpav tvevkssiag sstweryfip vscfltfnif dwlgrsltav fmwpgkdsrw
361 lpslvlarlv fvpllllcni kprryltvvf ehdawfiffm aafafsngyl aslcmcfgpk
421 kvkpaeaeta gaimafflcl glalgavfsf lfraiv
```

FIG. 1B

```
   1 gccatggccc gaggagacgc cccgcgggac agctaccacc tggtcgggat cagcttcttc
  61 atcctggggc tgggcaccct ccttccctgg aacttcttca tcaccgccat cccgtacttc
 121 caggcgcgac tggccggggc cggcaacagc acagccagga tcctgagcac caaccacacg
 181 ggtcccgagg atgccttcaa cttcaacaat tgggtgacgc tgctgtccca gctgcccctg
 241 ctgctcttca ccctcctcaa ctccttcctg taccagtgcg tcccggagac ggtgcgcatt
 301 ctgggcagcc tgctggccat actgctgctc tttgccctga cagcagcgct ggtcaaggtg
 361 gacatgagcc ccggaccctt cttctccatc accatggcct ccgtctgctt catcaactcc
 421 ttcagtgcag tcctacaggg cagcctcttc gggcagctgg gcaccatgcc ctccacctac
 481 agcaccctct tcctcagcgg ccagggcctg gctgggatct tgctgccct tgccatgctc
 541 ctgtccatgg ccagtggcgt ggacgccgag acctctgccc tggggtactt tatcacgccc
 601 tatgtgggca tcctcatgtc catcgtgtgt tacctgagcc tgcctcacct gaagtttgcc
 661 cgctactacc tggccaataa atcatcccag gcccaagctc aggagctgga gaccaaagct
 721 gagctcctcc agtctgatga acgggatt cccagtagtc cccagaaagt agctctgacc
 781 ctggatcttg acctggagaa ggagccggaa tcagagccag atgagcccca gaagccagga
 841 aaaccttcag tcttcactgt cttccagaag atctggctga cagcgctgtg ccttgtgttg
 901 gtcttcacag tcaccctgtc cgtcttcccc gccatcacag ccatggtgac cagctccacc
 961 agtcctggga gtggagtca gttcttcaac cccatctgct gcttcctcct cttcaacatc
1021 atggactggc tgggacggag cctgacctct tacttcctgt ggccagacga ggacagccgg
1081 ctgctgcccc tgctggtctg cctgcggttc ctgttcgtgc cctcttcat gctgtgccac
1141 gtgccccaga ggtcccggct gcccatcctc ttcccacagg atgcctactt catcaccttc
1201 atgctgctct tgccgtttc taatggctac ctggtgtccc tcaccatgtg cctggcgccc
1261 aggcaggtgc tgccacacga gagggaggtg gccggcgccc tcatgacctt cttcctggcc
1321 ctgggacttt cctgtggagc ctccctctcc ttcctcttca aggcgctgct ctgaagtggc
1381 ccctccaggc tctttggcag cctcttctcg acgtctcctt ccggagctga gatccagccc
1441 agggcgaatg gcgagcttgg ctcaggcctc tgcggggtgg aggcccctgg gcctgaggct
1501 gccagcagcg ggcaggagct gctcttcatc cacttggagt gctgcgggga agaaatcacc
1561 accggtcatt ctaacc
```

FIG. 2A

```
   1 margdaprds yhlvgisffi lglgtllpwn ffitaipyfq arlagagnst arilstnhtg
  61 pedafnfnnw vtllsqlpll lftllnsfly qcvpetvril gsllailllf altaalvkvd
 121 mspgpffsit masvcfinsf savlqgslfg qlgtmpstys tlflsgqgla gifaalamll
 181 smasgvdaet salgyfitpy vgilmsivcy lslphlkfar yylankssqa qaqeletkae
 241 llqsdengip sspqkvaltl dldlekepes epdepqkpgk psvftvfqki wltalclvlv
 301 ftvtlsvfpa itamvtssts pgkwsqffnp iccfllfnim dwlgrsltsy flwpdedsrl
 361 lpllvclrfl fvplfmlchv pqrsrlpilf pqdayfitfm llfavsngyl vsltmclapr
 421 qvlphereva galmtfflal glscgaslsf lfkall
```

FIG. 2B

Nucleotide and Amino Acid Sequences of mAb 3E10 VH

```
       FR1
       E   V   Q   L   V   E   S   G   G   G   L   V   K   P   G   G   S   R
3E10   GAGGTGCAGCTGGTGGAGTCTGGGGGAGGCTTAGTGAAGCCTGGAGGGTCCCGG

CDR1
       K   L   S   C   A   A   S   G   F   T   F   S   D   Y   G   M   H
3E10   AAACTCTCCTGTGCAGCCTCTGGATTCACTTTCAGT GACTATGGAATGCAC

FR2
       W   V   R   Q   A   P   E   K   G   L   E   W   V   A
3E10   TGGGTCCGTCAGGCTCCAGAGAAGGGGCTGGAGTGGGTTGCA

CDR2
       Y   I   S   S   G   S   S   T   I   Y   Y   A   D   T   V   K   G
3E10   TACATTAGTAGTGGCAGTAGTACCATCTACTATGCAGACACAGTGAAGGGC

FR3
       R   F   T   I   S   R   D   N   A   K   N   T   L   F   L   Q   M   T
3E10   CGATTCACCATCTCCAGAGACAATGCCAAGAACACCCTGTTCCTGCAAATGACC

S   L   R   S   E   D   T   A   M   Y   Y   C   A   R
3E10   AGTCTAAGGTCTGAGGACACAGCCATGTATTACTGTGCAAGG

CDR3                       FR4
       R   G   L   L   L   D   Y   W   G   Q   G   T   T   L   T   V   S   S
3E10   CGGGGGTTACTACTTGACTAC TGGGGCCAAGGCACCACTCTCACAGTCTCCTCA
```

FIG. 3

Nucleotide and Amino Acid Sequences of mAb 3E10 Vk

```
              FR1
              D   I   V   L   T   Q   S   P   A   S   L   A   V   S   L   G   Q   R
3E10VkIII     GACATTGTGCTGACACAGTCTCCTGCTTCCTTAGCTGTATCTCTGGGGCAGAGG

S   I   V   M   T   Q   T   P   K   F   L   P   V   S   A   G   D   R
3E10VkSER     AGTATTGTGATGACCCAGACTCCCAAATTCCTGCCTGTATCAGCAGGAGACAGG

CDR1
              A   T   I   S   C   R   A   S   K   S   V   S   T   S   S   Y   S   Y   M   H
3E10VkIII     GCCACCATCTCCTGC AGGGCCAGCAAAAGTGTCAGTACATCTAGCTATAGTTACATGCAC

V   T   M   T   C   K   A   S   Q   S   V   G   N   N   V   A
3E10VkSER     GTTACCATGACCTGC AAGGCCAGTCAGAGTGTGCGTAATAATGTAGCC

FR2
              W   Y   Q   Q   K   P   G   Q   P   P   K   L   L   I   K
3E10VkIII     TGGTACCAACAGAAACCAGGACAGCCACCCAAACTCCTCATCAAG

W   Y   Q   Q   K   P   G   Q   S   P   K   L   L   I   Y
3E10VkSER     TGGTACCAACAGAAGCCAGGACAGTCTCCTAAACTGCTGATATAC

CDR2                    FR3
              Y   A   S   Y   L   E   S   G   V   P   A   R   F   S   G   S   G
3E10VkIII     TATGCATCCTACCTAGAATCT   GGGGTTCCTGCCAGGTTCAGTGGCAGTGGG

Y   A   S   N   R   Y   T   G   V   P   D   R   F   T   G   S   G
3E10VkSER     TATGCATCCAATCGCTACACT   GGAGTCCCTGATCGCTTCACTGGCAGTGGA

S   G   T   D   F   T   L   N   I   H   P   V   E   E   E   D   A   A
3E10VkIII     TCTGGGACAGACTTTCACCTCAACATCCATCCTGTGGAGGAGGAGGATGCTGCA

S   G   T   D   F   T   F   T   I   S   S   V   Q   V   E   D   L   A
3E10VkSER     TCTGGGACAGATTTCACTTTCACCATCAGCAGTGTGCAGGTTGAAGACCTGGCA

CDR3                            FR4
              T   Y   Y   C   Q   Q   S   R   E   F   P   W   T   F   G   G   G
3E10VkIII     ACATATTACTGT    CAGCACAGTAGGGAGTTTCCGTGGACG     TTCGGTGGAGGC

V   Y   F   C   Q   Q   H   Y   S   S   P   W   T   F   G   G   G
3E10VkSER     GTTTATTTCTGT    CAGCAGCATTATAGCTCTCCGTGGACG     TTCGGTGGAGGC

T   K   L   E   L   K
3E10VkIII     ACCAAGCTGGAGTTGAAA

T   K   L   E   I   K
3E10VkSER     ACCAAGCTGGAAATCAAA
```

FIG. 4

SEQUENCE LISTING

```
<160> NUMBER OF SEQ ID NOS: 14

<210> SEQ ID NO 1
<211> LENGTH: 2162
<212> TYPE: DNA
<213> ORGANISM: Homo sapiens

<400> SEQUENCE: 1
gggctgcgct gtccagctgt ggctatggcc ccagccccga gatgaggagg gagagaacta      60
```

| | |
|---|---|
| ggggcccgca ggcctgggaa tttccgtccc ccaccaagtc cggatgctca ctccaaagtc | 120 |
| tcagcaggcc cctgagggag ggagctgtca gccagggaaa accgagaaca ccatcaccat | 180 |
| gacaaccagt caccagcctc aggacagata caaagctgtc tggcttatct tcttcatgct | 240 |
| gggtctggga acgctgctcc cgtggaattt tttcatgacg gccactcagt atttcacaaa | 300 |
| ccgcctggac atgtcccaga atgtgtcctt ggtcactgct gaactgagca aggacgccca | 360 |
| ggcgtcagcc gcccctgcag caccccttgcc tgagcggaac tctctcagtg ccatcttcaa | 420 |
| caatgtcatg accctatgtg ccatgctgcc cctgctgtta ttcacctacc tcaactcctt | 480 |
| cctgcatcag aggatccccc agtccgtacg atcctgggc agcctggtgg ccatcctgct | 540 |
| ggtgtttctg atcactgcca tcctggtgaa ggtgcagctg gatgctctgc ccttctttgt | 600 |
| catcaccatg atcaagatcg tgctcattaa ttcatttggt gccatcctgc agggcagcct | 660 |
| gtttggtctg gctggccttc tgcctgccag ctacacggcc cccatcatga gtggccaggg | 720 |
| cctagcaggc ttcttttgcct ccgtggccat gatctgcgct attgccagtg gctcggaact | 780 |
| atcagaaagt gccttcggct actttatcac agcctgtgct gttatcattt tgaccatcat | 840 |
| ctgttacctg ggcctgcccc gcctggaatt ctaccgctac taccagcagc tcaagcttga | 900 |
| aggacccggg gagcaggaga ccaagttgga cctcattagc aaaggagagg agccaagagc | 960 |
| aggcaaagag gaatctggag tttcagtctc caactctcag cccaccaatg aaagccactc | 1020 |
| tatcaaagcc atcctgaaaa atatctcagt cctggctttc tctgtctgct tcatcttcac | 1080 |
| tatcaccatt gggatgtttc agccgtgac tgttgaggtc aagtccagca tcgcaggcag | 1140 |
| cagcacctgg gaacgttact tcattcctgt gtcctgtttc ttgactttca atatctttga | 1200 |
| ctggttgggc cggagcctca cagctgtatt catgtggcct gggaaggaca gccgctggct | 1260 |
| gccaagcctg gtgctggccc ggctggtgtt tgtgccactg ctgctgctgt gcaacattaa | 1320 |
| gccccgccgc tacctgactg tggtcttcga gcacgatgcc tggttcatct tcttcatggc | 1380 |
| tgcctttgcc ttctccaacg gctacctcgc cagcctctgc atgtgcttcg ggcccaagaa | 1440 |
| agtgaagcca gctgaggcag agaccgcagg agccatcatg gccttcttcc tgtgtctggg | 1500 |
| tctggcactg ggggctgttt tctccttcct gttccgggca attgtgtgac aaaggatgga | 1560 |
| cagaaggact gcctgcctcc ctccctgtct gcctcctgcc ccttccttct gccagggtg | 1620 |
| atcctgagtg gtctggcggt tttttcttct aactgacttc tgctttccac ggcgtgtgct | 1680 |
| gggcccggat ctccaggccc tggggaggga gcctctggac ggacagtggg gacattgtgg | 1740 |
| gtttgggggct cagagtcgag ggacggggtg tagcctcggc atttgcttga gtttctccac | 1800 |
| tcttggctct gactgatccc tgcttgtgca ggccagtgga ggctcttggg cttggagaac | 1860 |
| acgtgtgtct ctgtgtatgt gtctgtgtgt ctgcgtccgt gtctgtcaga ctgtctgcct | 1920 |
| gtcctggggt ggctaggagc tgggtctgac cgttgtatgg tttgacctga tatactccat | 1980 |
| tctcccctgc gcctcctcct ctgtgttttt tccatgtccc cctcccaact ccccatgccc | 2040 |
| agttttttacc catcatgcac cctgtacagt tgccacgtta ctgcctttt taaaaatata | 2100 |
| tttgacagaa accaggtgcc ttcagaggct ctctgattta aataaacctt tcttgttttt | 2160 |
| tt | 2162 |

<210> SEQ ID NO 2
<211> LENGTH: 456
<212> TYPE: PRT
<213> ORGANISM: Homo sapiens

<400> SEQUENCE: 2

```
Met Thr Thr Ser His Gln Pro Gln Asp Arg Tyr Lys Ala Val Trp Leu
1               5                   10                  15
Ile Phe Phe Met Leu Gly Leu Gly Thr Leu Leu Pro Trp Asn Phe Phe
                20                  25                  30
Met Thr Ala Thr Gln Tyr Phe Thr Asn Arg Leu Asp Met Ser Gln Asn
            35                  40                  45
Val Ser Leu Val Thr Ala Glu Leu Ser Lys Asp Ala Gln Ala Ser Ala
    50                  55                  60
Ala Pro Ala Ala Pro Leu Pro Glu Arg Asn Ser Leu Ser Ala Ile Phe
65                  70                  75                  80
Asn Asn Val Met Thr Leu Cys Ala Met Leu Pro Leu Leu Leu Phe Thr
                85                  90                  95
Tyr Leu Asn Ser Phe Leu His Gln Arg Ile Pro Gln Ser Val Arg Ile
                100                 105                 110
Leu Gly Ser Leu Val Ala Ile Leu Leu Val Phe Leu Ile Thr Ala Ile
            115                 120                 125
Leu Val Lys Val Gln Leu Asp Ala Leu Pro Phe Phe Val Ile Thr Met
    130                 135                 140
Ile Lys Ile Val Leu Ile Asn Ser Phe Gly Ala Ile Leu Gln Gly Ser
145                 150                 155                 160
Leu Phe Gly Leu Ala Gly Leu Leu Pro Ala Ser Tyr Thr Ala Pro Ile
                165                 170                 175
Met Ser Gly Gln Gly Leu Ala Gly Phe Phe Ala Ser Val Ala Met Ile
                180                 185                 190
Cys Ala Ile Ala Ser Gly Ser Glu Leu Ser Glu Ser Ala Phe Gly Tyr
                195                 200                 205
Phe Ile Thr Ala Cys Ala Val Ile Ile Leu Thr Ile Ile Cys Tyr Leu
                210                 215                 220
Gly Leu Pro Arg Leu Glu Phe Tyr Arg Tyr Tyr Gln Gln Leu Lys Leu
225                 230                 235                 240
Glu Gly Pro Gly Glu Gln Glu Thr Lys Leu Asp Leu Ile Ser Lys Gly
                245                 250                 255
Glu Glu Pro Arg Ala Gly Lys Glu Glu Ser Gly Val Ser Val Ser Asn
                260                 265                 270
Ser Gln Pro Thr Asn Glu Ser His Ser Ile Lys Ala Ile Leu Lys Asn
                275                 280                 285
Ile Ser Val Leu Ala Phe Ser Val Cys Phe Ile Phe Thr Ile Thr Ile
                290                 295                 300
Gly Met Phe Pro Ala Val Thr Val Glu Val Lys Ser Ser Ile Ala Gly
305                 310                 315                 320
Ser Ser Thr Trp Glu Arg Tyr Phe Ile Pro Val Ser Cys Phe Leu Thr
                325                 330                 335
Phe Asn Ile Phe Asp Trp Leu Gly Arg Ser Leu Thr Ala Val Phe Met
                340                 345                 350
Trp Pro Gly Lys Asp Ser Arg Trp Leu Pro Ser Leu Val Leu Ala Arg
                355                 360                 365
Leu Val Phe Val Pro Leu Leu Leu Cys Asn Ile Lys Pro Arg Arg
                370                 375                 380
Tyr Leu Thr Val Val Phe Glu His Asp Ala Trp Phe Ile Phe Phe Met
385                 390                 395                 400
Ala Ala Phe Ala Phe Ser Asn Gly Tyr Leu Ala Ser Leu Cys Met Cys
                405                 410                 415
```

Phe Gly Pro Lys Lys Val Lys Pro Ala Glu Ala Glu Thr Ala Gly Ala
            420                 425                 430

Ile Met Ala Phe Phe Leu Cys Leu Gly Leu Ala Leu Gly Ala Val Phe
        435                 440                 445

Ser Phe Leu Phe Arg Ala Ile Val
    450                 455

<210> SEQ ID NO 3
<211> LENGTH: 1576
<212> TYPE: DNA
<213> ORGANISM: Homo sapiens

<400> SEQUENCE: 3

```
gccatggccc gaggagacgc cccgcgggac agctaccacc tggtcgggat cagcttcttc      60
atcctggggc tgggcaccct ccttccctgg aacttcttca tcaccgccat cccgtacttc     120
caggcgcgac tggccggggc cggcaacagc acagccagga tcctgagcac caaccacacg     180
ggtcccgagg atgccttcaa cttcaacaat tgggtgacgc tgctgtccca gctgcccctg     240
ctgctcttca ccctcctcaa ctccttcctg taccagtgcg tcccggagac ggtgcgcatt     300
ctgggcagcc tgctggccat actgctgctc tttgccctga cagcagcgct ggtcaaggtg     360
gacatgagcc ccggaccctt cttctccatc accatggcct ccgtctgctt catcaactcc     420
ttcagtgcag tcctacaggg cagcctcttc gggcagctgg gcaccatgcc ctccacctac     480
agcaccctct tcctcagcgg ccagggcctg gctgggatct tgctgcccct tgccatgctc     540
ctgtccatgg ccagtggcgt ggacgccgag acctctgccc tggggtactt tatcacgccc     600
tatgtgggca tcctcatgtc catcgtgtgt tacctgagcc tgcctcacct gaagtttgcc     660
cgctactacc tggccaataa atcatcccag gcccaagctc aggagctgga gaccaaagct     720
gagctcctcc agtctgatga gaacgggatt cccagtagtc cccagaaagt agctctgacc     780
ctggatcttg acctggagaa ggagccggaa tcagagccag atgagcccca gaagccagga     840
aaaccttcag tcttcactgt cttccagaag atctggctga cagcgctgtg ccttgtgttg     900
gtcttcacag tcaccctgtc cgtcttcccc gccatcacag ccatggtgac cagctccacc     960
agtcctggga gtggagtca gttcttcaac cccatctgct gcttcctcct cttcaacatc    1020
atggactggc tgggacggag cctgacctct tacttcctgt ggccagacga ggacagccgg    1080
ctgctgcccc tgctggtctg cctgcggttc ctgttcgtgc ccctcttcat gctgtgccac    1140
gtgccccaga ggtcccggct gcccatcctc ttcccacagg atgcctactt catcaccttc    1200
atgctgctct tgccgtttc taatggctac ctggtgtccc tcaccatgtg cctggcgccc    1260
aggcaggtgc tgccacacga gagggaggtg gccggcgccc tcatgacctt cttcctggcc    1320
ctgggactt cctgtggagc ctccctctcc ttcctcttca ggcgctgct ctgaagtggc    1380
ccctccaggc tctttggcag cctcttctcg acgtctcctt ccggagctga gatccagccc    1440
agggcgaatg gcgagcttgg ctcaggcctc tgcggggtgg aggcccctgg gcctgaggct    1500
gccagcagcg ggcaggagct gctcttcatc cacttggagt gctgcgggga agaaatcacc    1560
accggtcatt ctaacc                                                   1576
```

<210> SEQ ID NO 4
<211> LENGTH: 456
<212> TYPE: PRT
<213> ORGANISM: Homo sapiens

<400> SEQUENCE: 4

-continued

```
Met Ala Arg Gly Asp Ala Pro Arg Asp Ser Tyr His Leu Val Gly Ile
1               5                  10                 15

Ser Phe Phe Ile Leu Gly Leu Gly Thr Leu Leu Pro Trp Asn Phe Phe
            20                 25                 30

Ile Thr Ala Ile Pro Tyr Phe Gln Ala Arg Leu Ala Gly Ala Gly Asn
            35                 40                 45

Ser Thr Ala Arg Ile Leu Ser Thr Asn His Thr Gly Pro Glu Asp Ala
50                  55                 60

Phe Asn Phe Asn Asn Trp Val Thr Leu Leu Ser Gln Leu Pro Leu Leu
65                  70                 75                 80

Leu Phe Thr Leu Leu Asn Ser Phe Leu Tyr Gln Cys Val Pro Glu Thr
                85                 90                 95

Val Arg Ile Leu Gly Ser Leu Leu Ala Ile Leu Leu Leu Phe Ala Leu
                100                105                110

Thr Ala Ala Leu Val Lys Val Asp Met Ser Pro Gly Pro Phe Phe Ser
            115                120                125

Ile Thr Met Ala Ser Val Cys Phe Ile Asn Ser Phe Ser Ala Val Leu
            130                135                140

Gln Gly Ser Leu Phe Gly Gln Leu Gly Thr Met Pro Ser Thr Tyr Ser
145                 150                155                160

Thr Leu Phe Leu Ser Gly Gln Gly Leu Ala Gly Ile Phe Ala Ala Leu
                165                170                175

Ala Met Leu Leu Ser Met Ala Ser Gly Val Asp Ala Glu Thr Ser Ala
            180                185                190

Leu Gly Tyr Phe Ile Thr Pro Tyr Val Gly Ile Leu Met Ser Ile Val
            195                200                205

Cys Tyr Leu Ser Leu Pro His Leu Lys Phe Ala Arg Tyr Tyr Leu Ala
210                 215                220

Asn Lys Ser Ser Gln Ala Gln Ala Gln Glu Leu Glu Thr Lys Ala Glu
225                 230                235                240

Leu Leu Gln Ser Asp Glu Asn Gly Ile Pro Ser Ser Pro Gln Lys Val
                245                250                255

Ala Leu Thr Leu Asp Leu Asp Leu Glu Lys Glu Pro Glu Ser Glu Pro
            260                265                270

Asp Glu Pro Gln Lys Pro Gly Lys Pro Ser Val Phe Thr Val Phe Gln
            275                280                285

Lys Ile Trp Leu Thr Ala Leu Cys Leu Val Leu Val Phe Thr Val Thr
            290                295                300

Leu Ser Val Phe Pro Ala Ile Thr Ala Met Val Thr Ser Ser Thr Ser
305                 310                315                320

Pro Gly Lys Trp Ser Gln Phe Phe Asn Pro Ile Cys Cys Phe Leu Leu
            325                330                335

Phe Asn Ile Met Asp Trp Leu Gly Arg Ser Leu Thr Ser Tyr Phe Leu
            340                345                350

Trp Pro Asp Glu Asp Ser Arg Leu Leu Pro Leu Leu Val Cys Leu Arg
            355                360                365

Phe Leu Phe Val Pro Leu Phe Met Leu Cys His Val Pro Gln Arg Ser
370                 375                380

Arg Leu Pro Ile Leu Phe Pro Gln Asp Ala Tyr Phe Ile Thr Phe Met
385                 390                395                400

Leu Leu Phe Ala Val Ser Asn Gly Tyr Leu Val Ser Leu Thr Met Cys
                405                410                415

Leu Ala Pro Arg Gln Val Leu Pro His Glu Arg Glu Val Ala Gly Ala
```

```
                420             425             430
Leu Met Thr Phe Phe Leu Ala Leu Gly Leu Ser Cys Gly Ala Ser Leu
        435                 440                 445

Ser Phe Leu Phe Lys Ala Leu Leu
    450                 455

<210> SEQ ID NO 5
<211> LENGTH: 348
<212> TYPE: DNA
<213> ORGANISM: Mus musculus

<400> SEQUENCE: 5
gaggtgcagc tggtggagtc tgggggaggc ttagtgaagc ctggagggtc ccggaaactc      60
tcctgtgcag cctctggatt cactttcagt gactatggaa tgcactgggt ccgtcaggct     120
ccagagaagg ggctggagtg ggttgcatac attagtagtg gcagtagtac catctactat     180
gcagacacag tgaagggccg attcaccatc tccagagaca atgccaagaa caccctgttc     240
ctgcaaatga ccagtctaag gtctgaggac acagccatgt attactgtgc aaggcggggg     300
ttactacttg actactgggg ccaaggcacc actctcacag tctcctca                  348

<210> SEQ ID NO 6
<211> LENGTH: 116
<212> TYPE: PRT
<213> ORGANISM: Mus musculus

<400> SEQUENCE: 6

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 7
<211> LENGTH: 333
<212> TYPE: DNA
<213> ORGANISM: Mus musculus

<400> SEQUENCE: 7
gacattgtgc tgacacagtc tcctgcttcc ttagctgtat ctctggggca gagggccacc      60
atctcctgca gggccagcaa aagtgtcagt acatctagct atagttacat gcactggtac     120
caacagaaac caggacagcc acccaaactc ctcatcaagt atgcatccta cctagaatct     180
ggggttcctg ccaggttcag tggcagtggg tctgggacag actttcacct caacatccat     240
cctgtggagg aggaggatgc tgcaacatat tactgtcagc acagtaggga gtttccgtgg     300
acgttcggtg gaggcaccaa gctggagttg aaa                                  333
```

<210> SEQ ID NO 8
<211> LENGTH: 111
<212> TYPE: PRT
<213> ORGANISM: Mus musculus

<400> SEQUENCE: 8

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110
```

<210> SEQ ID NO 9
<211> LENGTH: 321
<212> TYPE: DNA
<213> ORGANISM: Mus musculus

<400> SEQUENCE: 9

```
agtattgtga tgacccagac tcccaaattc ctgcctgtat cagcaggaga cagggttacc     60
atgacctgca aggccagtca gagtgtgggt aataatgtag cctggtacca acagaagcca    120
ggacagtctc ctaaactgct gatatactat gcatccaatc gctacactgg agtccctgat    180
cgcttcactg gcagtggatc tgggacagat ttcactttca ccatcagcag tgtgcaggtt    240
gaagacctgg cagtttattt ctgtcagcag cattatagct ctccgtggac gttcggtgga    300
ggcaccaagc tggaaatcaa a                                             321
```

<210> SEQ ID NO 10
<211> LENGTH: 107
<212> TYPE: PRT
<213> ORGANISM: Mus musculus

<400> SEQUENCE: 10

```
Ser Ile Val Met Thr Gln Thr Pro Lys Phe Leu Pro Val Ser Ala Gly
1               5                   10                  15

Asp Arg Val Thr Met Thr Cys Lys Ala Ser Gln Ser Val Gly Asn Asn
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Trp
                85                  90                  95

Thr Phe Gly Gly Gly Thr Lys Leu Glu Ile Lys
            100                 105
```

```
<210> SEQ ID NO 11
<211> LENGTH: 5
<212> TYPE: PRT
<213> ORGANISM: Artificial sequence
<220> FEATURE:
<223> OTHER INFORMATION: Synthetic construct

<400> SEQUENCE: 11

Gly Gly Gly Gly Ser
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic construct

<400> SEQUENCE: 12

His His His His His His
1               5

<210> SEQ ID NO 13
<211> LENGTH: 10
<212> TYPE: PRT
<213> ORGANISM: Artificial sequence
<220> FEATURE:
<223> OTHER INFORMATION: Synthetic construct

<400> SEQUENCE: 13

Gly Phe Pro Arg Gly Phe Pro Ala Gly Gly
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic construct

<400> SEQUENCE: 14

Thr Arg His Arg Gln Pro Arg Gly Trp Glu Gln Leu
1               5                   10
```

INTRANUCLEAR PROTEIN TRANSDUCTION THROUGH A NUCLEOSIDE SALVAGE PATHWAY

CROSS-REFERENCE TO RELATED APPLICATIONS

This application is a continuation application of U.S. application Ser. No. 12/126,810 filed May 23, 2008, now issued as U.S. Pat. No. 8,956,825; which claims the benefit under 35 USC § 119(e) to U.S. Application Ser. No. 60/931,855 filed May 24, 2007, now expired. The disclosure of each of the prior applications is considered part of and is incorporated by reference in the disclosure of this application.

GRANT INFORMATION

This invention was made with government support by the U.S. Department of Veterans Affairs. The government has certain rights in the invention.

BACKGROUND OF THE INVENTION

1. Field of the Invention

The present invention relates generally to conjugate molecules and more specifically, to conjugate molecules and their use in the delivery of active agents into cells using endogenous cellular transport pathways.

2. Background Information

Transporter proteins are involved in the cellular uptake of various molecules into and/or through cells. Carrier-mediated transport systems use proteins that are anchored to the cell membrane, typically by a plurality of membrane-spanning domains and function by transporting their substrates via active or passive mechanisms. Carrier-mediated transport systems are involved in the active or non-active, facilitated transport of many important nutrients such as vitamins, sugars, and amino acids. Carrier-mediated transporters are also present in organs such as the liver and kidney, in which the proteins are involved in the excretion or re-absorption of circulating compounds. Polar or hydrophilic compounds typically diffuse poorly across the lipid bilayers that constitute cellular membranes. For many small molecules (e.g., amino acids, di- and tripeptides, monosaccharides, nucleosides and water-soluble vitamins) there exist specific carrier-mediated transporters for active transport of the solute molecules across biological membranes.

The uptake or release physiological nucleosides and many of their synthetic analogs by mammalian cells occurs primarily by means of specific carrier-mediated transporters known as nucleoside transporters. Nucleoside transporters have been classified into two categories: (i) equilibrative (facilitated diffusion) and (ii) concentrative (secondary active) sodium-dependent. Two equilibrative transport systems with similar broad substrate specificities have been identified and designated as the es (equilibrative sensitive) and ei (equilibrative insensitive) transporters, on the basis of their sensitivity or insensitivity to inhibition by nitrobenzyl-thioinosine (NBMPR, 1), respectively. As many as six sodium ion-coupled (concentrative) nucleoside transport systems designated cif/N1, cit/N2, cib/N3, cit/N4, cs/N5 and csg/N6 have also been functionally identified in mammalian tissues.

The anti-DNA antibody fragment 3E10 Fv has been demonstrated to be a novel molecular delivery vehicle due to its penetration into living cells with specific nuclear localization, absence of toxicity, and successful delivery of therapeutic cargo proteins in vitro and in vivo. Elucidation of the pathway that allows 3E10 Fv to cross cell membranes is critical to the development of new molecular therapies, which rely on the regulation of gene expression by intranuclear transduction of macromolecules.

SUMMARY OF THE INVENTION

The present invention is based on the discovery that a DNA-binding antibody that can penetrate cells and localize into the nucleus is transported by a nucleoside transport pathway.

According to one embodiment of the invention, there are provided conjugates including a substrate that is capable of being transported by a nucleoside transport pathway, and an active agent linked to the substrate, wherein the conjugate is transported by the nucleoside transport pathway. In particular embodiments in which the substrate is an antibody, the antibody is not the monoclonal antibody 3E10 or a fragment thereof. In certain embodiments, the nucleoside transport pathway includes an equilibrative nucleoside transporter or a concentrative nucleoside transporter. In embodiments in which the nucleoside transport pathway involves an equilibrative nucleoside transporter, such a transporter may be insensitive to inhibition by low concentrations of nitrobenzylmercaptopurine riboside (NBMBR).

According to another embodiment of the invention, there are provided methods for delivering a conjugate to a target cell expressing a nucleoside transport pathway. Such methods involve contacting the target cell expressing the nucleoside transport pathway with a conjugate including a substrate that is capable of being transported by a nucleoside transport pathway, and an active agent linked to the substrate, wherein the conjugate is transported by the nucleoside transport pathway. In particular embodiments in which the substrate is an antibody, the antibody is not the monoclonal antibody 3E10 or a fragment thereof. In certain embodiments, the nucleoside transport pathway includes an equilibrative nucleoside transporter or a concentrative nucleoside transporter. In embodiments in which the nucleoside transport pathway involves an equilibrative nucleoside transporter, such a transporter may be insensitive to inhibition by low concentrations of nitrobenzylmercaptopurine riboside (NBMBR).

According to a further embodiment of the invention, there are provided methods of screening a conjugate for transport by a nucleoside transport pathway. Such methods include, contacting a cell expressing the nucleoside transport pathway, with a conjugate under suitable conditions for transport to occur; and determining whether the conjugate is transported into the cell by the nucleoside transport pathway. In certain embodiments, the determining step includes comparing the amount of conjugate transported into a cell expressing the nucleoside transport system to the amount of conjugate transported into a control cell not expressing the nucleoside transport system. In these embodiments, an increase in transport of conjugate of the cell expressing the nucleoside transport pathway as compared to the control cell indicates transport is by that nucleoside transport pathway.

According to yet another embodiment of the invention, there are provided methods for treating a disease or disorder in a cell or tissue expressing a nucleoside transport pathway. The method includes administering to a patient having the disease or disorder a conjugate including a substrate that is capable of being transported by the nucleoside transport pathway expressed in the affected cell or tissue and an active agent for treating disease or disorder, wherein the conjugate is also transported by the nucleoside transport pathway. In this way, the conjugate is transported into the affected cells or tissue, thereby delivering the active agent. In certain embodiments the disease or disorder involves skeletal muscle and the conjugate is transported into the skeletal muscle cells, thereby delivering the active agent.

According to yet another embodiment, there are provided methods for treating a genetic disorder wherein the method includes, administering to a patient having a genetic disorder a conjugate including: a substrate that is capable of being transported by an equilibrative nucleoside transporter, and an active agent for treating the genetic disorder, wherein the active agent is linked to the substrate, and further wherein the conjugate is transported by the equilibrative nucleoside transporter, whereby the conjugate is transported into cells, thereby delivering the active agent. In certain embodiments, the active agent is a gene or protein that is deficient in patients having the genetic disease.

In other aspects, this disclosure provides a method of treating a cancer, wherein the method includes, administering to a patient having cancer a conjugate including: a substrate that is capable of being transported by an equilibrative nucleoside transporter, and an active agent for treating cancer, wherein the active agent is linked to the substrate, and further wherein the conjugate is transported by the equilibrative nucleoside transporter, whereby the conjugate is transported into cancerous cells, thereby delivering the active agent. In certain embodiments, the active agent is a tumor suppressor gene or tumor suppressor protein.

According to still another embodiment of the invention, there are provided methods of treating an autoimmune disorder including administering to a patient having the autoimmune disorder a compound that inhibits transport by a nucleoside transport pathway.

The present disclosure also provides a pharmaceutical composition including a conjugate described herein and an agent that promotes ENT2 expression in a tissue. In some aspects, the agent that promotes ENT2 expression in a tissue is an agent that treats or inhibits hypoxia or an agent that inhibits HIF-1. The tissue may be a hypoxic tissue, such as a hypoxic tumor, a tissue with insufficient vasculature, an ulcer, a diabetic ulcer, a poorly-healing wound, an ischemic area, an ischemic area resulting from stroke, or an ischemic area resulting from cardiovascular disease. In certain embodiments, the agent that inhibits HIF-1α is a siRNA, an RNAi construct, a hairpin RNA, or a miRNA that reduces HIF-1α expression. In some embodiments, the HIF-1α inhibitor is a chemotherapeutic drug, topotecan, NSC 644221, PX-478, YC-1, 17-AAG, or bevacizumab. In certain embodiments, the agent that treats or inhibits hypoxia is an agent that normalizes tumor vasculature, or an agent that alters the redox state of a tissue. The agent that treats or inhibits hypoxia may be excess oxygen, TSC, or almitrine.

Furthermore, herein is provided a method of treating an ENT-2 deficient tissue, wherein the method includes: a) administering an agent that promotes ENT2 expression and/or activity, and b) administering one of the conjugates disclosed herein.

BRIEF DESCRIPTION OF THE DRAWINGS

FIGS. 1A and 1B show the nucleotide sequence (SEQ ID NO:1; GenBank Accession No. U81375) and amino acid sequence (SEQ ID NO:2; GenBank Accession No. AAC511030.1) of human ENT1, respectively.

FIGS. 2A and 2B show the nucleotide sequence (SEQ ID NO:3; GenBank Accession No. AF029358) and amino acid sequence (SEQ ID NO:4; GenBank Accession No. AAC39526.1) of human ENT2, respectively.

FIG. 3 shows the nucleotide sequence (SEQ ID NO:5; GenBank Accession No. L16982) and amino acid sequence (SEQ ID NO:6) of mAb 3E10 $V_H$.

FIG. 4 shows the nucleotide and amino acid sequences of mAb 3E10 Vk light chains, 3E10VkIII (GenBank Accession No. L34051; SEQ ID NOs:7 and 8, for nucleotide and amino acid sequences, respectively) and 3E10VkSER (GenBank Accession No. L16981; SEQ ID NOs:9 and 10, for nucleotide and amino acid sequences, respectively).

DETAILED DESCRIPTION OF THE INVENTION

Before the present methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs.

In accordance with the present invention, there are provided conjugates containing a substrate that is capable of being transported by a nucleoside transport pathway, and an active agent linked to the substrate, wherein the conjugate is transported by the nucleoside transport pathway. In this way, the conjugate, and thus, the active agent, is transported into the target cell. In particular embodiments in which the substrate is an antibody, the antibody is not the monoclonal antibody 3E10 or a fragment thereof. In certain embodiments, the nucleoside transport pathway includes an equilibrative nucleoside transporter or a concentrative nucleoside transporter. In embodiments in which the nucleoside transport pathway involves an equilibrative nucleoside transporter, such a transporter may be insensitive to inhibition by low concentrations of nitrobenzylmercaptopurine riboside (NBMBR).

"Nucleoside transport pathways" refer to systems of one or more transport proteins that effect the transport of a substrate across one or more biological membranes. For example, a nucleoside transport pathway may mediate the step-wise transport of a substrate across the plasma membrane followed by the transport of the substrate across the membrane of an intracellular organelle. The transport proteins or nucleoside transporters responsible for such a step-wise translocation of a substrate across two biological membranes may be the same type of nucleoside transporter or may be of different types. In certain embodiments, the nucleoside transporter may be an equilibrative nucleoside transporter. In other embodiments, the nucleoside transporter may be a concentrative nucleoside transporter.

A "transport protein" or "transporter" is a protein that has a direct or indirect role in transporting a molecule across a membrane. The term includes, for example, membrane-bound proteins that recognize a substrate and effects its entry into, or exit from a cell by a carrier-mediated transporter or by receptor-mediated transport. Transporters may be present on plasma membranes or the membranes of intracellular organelles. Thus, transporters facilitate the transport of molecules into the cytoplasm or into an intracellular organelle.

Two different families of nucleoside transporters (NTs) have been characterized: equilibrative nucleoside transporters and concentrative nucleoside transporters. "Equilibrative nucleoside transporters" or "ENTs" refer to transporters that translocate substrate down the substrate's concentration gradient via passive transport or facilitated diffusion. ENT activity does not require a sodium ion (or other ion) gradient and are therefore termed "Na$^+$-independent" transporters. ENTs are categorized into one of two subtypes based on sensitivity to inhibition by nitrobenzylmercaptopurine riboside (NBMBR). One subtype of ENT (equilibrative, sensitive or "es"), is inhibited by ≤1 nM NBMPR, whereas the other subtype (equilibrative, insensitive or "ei"), is unaffected by low concentrations (e.g., <1 μM) of NBMPR.

Four members of the ENT family have been cloned and are termed ENT1, ENT2, ENT3, and ENT4. All 4 transport adenosine but differ from each other with respect to their ability to transport other nucleosides or nucleobases. ENT1 is an es subtype transporter. Exemplary polynucleotide sequences encoding human ENT1 include GenBank Accession No. U81375 and GenBank Accession No. AAC51103.1 represents the corresponding amino acid sequence. ENT1 is ubiquitously expressed in human and rodent tissues, although expression levels vary between tissues. ENT1 is known to transport a wide range of purine and pyrimidine nucleosides.

ENT2 is an ei subtype transporter. Exemplary polynucleotide sequences encoding human ENT2 include GenBank Accession No. AF029358 and GenBank Accession No. AAC39526 represents the corresponding amino acid sequence. ENT2 is expressed in a wide range of human and rodent tissues, including vascular endothelium, heart, brain, placenta, thymus, pancreas, prostate, kidney, and muscle, skeletal muscle, cardiac muscle, blood, skin, and ENT2-expressing cancer cells. ENT2-expressing cancer cells include, for example, certain renal tumor cells, breast tumor cells, prostate cancer cells, colon cancer cells, stomach cancer cells, leukemia cells, lung cancer cells, and ovarian cancer cells. Other types of ENT-2 expressing cancer cells are known in the art; for example see Lu X et al., Journal of Experimental Therapeutics and Oncology 2:200-212, 2002, and Pennycooke M et al., Biochemical and Biophysical Research Communications 208, 951-959, 2001. ENT2 exhibits high expression levels in skeletal muscle. ENT2 is also expressed in the membrane of organelles such as the nucleus. ENT2 is known to transport a wide range of purine and pyrimidine nucleosides and nucleobases.

ENT3 is an ei subtype transporter. Exemplary polynucleotide sequences encoding human ENT3 include GenBank Accession No. NM_018344 and GenBank Accession No. NP_060814representss the corresponding amino acid sequence. ENT3 is widely expressed in different tissues and is abundant in placenta. ENT3 appears to be predominantly an intracellular protein and co-localizes with lysosomal markers in cultured cells. ENT3 is known to transport a wide range of purine and pyrimidine nucleosides.

ENT4 is weakly inhibited by NBMPR. Exemplary polynucleotide sequences encoding human ENT4 include GenBank Accession No. BC047592 and GenBank Accession No. AAH47592 represents the corresponding amino acid sequence. ENT4 is fairly ubiquitously expressed and is abundant in brain, skeletal muscle, and heart. ENT4 is also substantially expressed in intestine, pancreas, kidney, liver, bone marrow, and lymph node. ENT4 is known to transport a wide range of purine and pyrimidine nucleosides and serotonin.

"Concentrative nucleoside transporters" or "CNTs" refer to a group of nucleoside transporters that transport nucleosides and nucleoside analogs by active transport. CNTs employ sodium gradients resulting from a difference in intracellular versus extracellular sodium concentration. This concentration gradient allows an uphill or concentrative transport of substrate across biological membranes. In general, the sodium concentration gradient across mammalian cell membranes favors movement of sodium and nucleoside into the cell. CNTs are therefore considered "Na$^+$-dependent" transporters. There are currently three cloned members of the CNT family and differ from each other with respect to substrate selectivity and substrate to sodium ratio.

CNT1 is known to transport pyrimidine nucleosides as well as adenosine, the latter in a high-affinity, low-capacity manner. Transport via CNT1 occurs at a ratio of 1:1 sodium-to-nucleoside ratio. Exemplary polynucleotide sequences encoding human CNT1 include GenBank Accession No. U62968 and GenBank Accession No. AAB53839.1 represents the corresponding amino acid sequence. CNT1 is primarily expressed in epithelial cells of tissues, such as small intestine, kidney, and liver, as well as in many regions of the brain.

CNT2 is known to transport purine nucleosides as well as uridine. Transport via CNT2 occurs at a ratio of 1:1 sodium-to-nucleoside ratio. Exemplary polynucleotide sequences encoding human CNT2 include GenBank Accession No. AF036109 and GenBank Accession No. AAB88539 represents the corresponding amino acid sequence. CNT2 is expressed in a wide range of human tissues such as the heart, liver, kidney, brain, placenta, pancreas, skeletal muscle, colon, and the small intestine.

CNT3 is known to be broadly selective, transporting purine and pyrimidine nucleosides, as well as various nucleoside analogs. Transport via CNT3 occurs at a ratio of 2:1 sodium-to-nucleoside ratio. Exemplary polynucleotide sequences encoding human CNT3 include GenBank Accession No. AF305210 and GenBank Accession No. AAG22551 represents the corresponding amino acid sequence. CNT3 is expressed in tissues such as the trachea, pancreas, bone marrow, and mammary gland, as well as in low levels in the intestine, lung, placenta, prostate, testis, and liver.

A "conjugate" as used herein generally refers to a molecule which contains a substrate that is capable of being transported by a nucleoside transport pathway linked to an active agent. The conjugate is also capable of being transported by a nucleoside transporter.

A "substrate" of a transport protein, as used generally herein, is a compound whose uptake into a cell or organelle is facilitated by the transport protein. Substrates have characteristic kinetic parameters (e.g., $V_{max}$ and $K_m$) for a particular transporter. $V_{max}$ refers to the number of molecules of substrate transported per unit time at saturating concentration of the substrate. $K_m$ refers to the concentration of the substrate at which the substrate is transported at half of $V_{max}$. In general, a high value of $V_{max}$ is desirable for a substrate of a transporter. A low value of $K_m$ is desirable for transport of low concentrations of a compound, and a high value of $K_m$ is desirable for transport of high concentrations of a compound. $V_{max}$ is affected both by the intrinsic turnover rate of a transporter (molecules/transporter protein) and transporter density in plasma membrane that depends on expression level. For these reasons, the intrinsic capacity of a compound to be transported by a particular transporter is usually expressed as the ratio $V_{max}$ of the compound/$V_{max}$ of a control compound known to be a substrate for the transporter.

A "substrate that is capable of being transported by a nucleoside transport pathway" refers to a molecule compound whose uptake into a cell or organelle is facilitated by a nucleoside transport protein or nucleoside transporter. Substrates used in the invention conjugates may be known substrates of nucleoside transporters or may be identified using methods known in the art and provided herein. Substrates may include a nucleoside, a nucleobase, a nucleotide, a nucleoside analog, an oligonucleotide, a peptide, a polypeptide, an antibody, an antibody fragment.

The term "nucleobase" refers to purine or pyrimidine bases. Examples include adenine, cytosine, guanine, uracil, and thymine. Nucleobases include modified bases, such as pseudouridine, dihydrouridine, inosine, ribothymidine, 7-methylguanosine (m7G), hypoxanthine, and xanthine.

The term "nucleoside" refers to a purine or pyrimidine base that is covalently linked to a 5-carbon sugar (i.e., pentose). When the sugar is ribose, the nucleoside is a ribonucleoside; when it is 2-deoxyribose, the nucleoside is a deoxyribonucleoside. Exemplary nucleosides include cytidine, uridine, adenosine, guanosine, and thymidine, and the corresponding deoxyribonucleosides, which form the basis of the nucleotides that form DNA and RNA.

The term "nucleoside analog" as used herein refers to a nucleoside in which the base moiety, the sugar moiety or both has been modified. Such analogs are generally synthetic and mimic natural nucleosides so that they may take the place of a nucleoside in cellular functions. For example, nucleosides may be incorporated into DNA or RNA in place of the natural corresponding nucleoside. Certain nucleoside analogs so incorporated can, for example, prevent further elongation of the nucleic acid chain during synthesis. Many nucleoside analogs have anti-viral or anti-cancer properties. Examples of nucleoside analogs include inosine, deoxyadenosine analogs such as didanosine (2',3'-dideoxyinosine, ddI) and vidarabine (9-β-D-ribofuranosyladenine), deoxycytidine analogs such as cytarabine (cytosine arabinoside, emtricitabine, lamivudine (2',3'-dideoxy-3'-thiacytidine, 3TC), and zalcitabine (2'-3'-dideoxycytidine, ddC), deoxyguanosine analogs such as abacavir, (deoxy-)thymidine analogs such as stavudine (2'-3'-didehydro-2'-3'-dideoxythymidine, d4T) and zidovudine (azidothymidine, or AZT), and deoxyuridine analogs such as idoxuridine and trifluridine.

As used herein, the phrase "active agent" refers to a molecule that has a biological effect in a cell. In certain embodiments the active agent may be a nucleic acid, an inorganic molecule, an organic molecule, a small organic molecule, a drug compound, a peptide, a polypeptide, an antibody, an antibody fragment, a peptidomimetic, a lipid, DNA, RNA, a ribozyme, hairpin RNA, siRNA (small interfering RNAs) of varying chemistries, miRNA, an antagomir, a PNA (peptide nucleic acid), an LNA (locked nucleic acids), or a morpholino. In certain embodiments, the active agent is a polypeptide.

In other embodiments, the active agent is selected from the group consisting of α-glucosidase, α-L-iduronidase, α-galactosidase A, arylsulfatase, N-acetylgalactosamine-6-sulfatase or β-galactosidase, iduronate 2-sulfatase, ceramidase, galactocerebrosidase, β-glucuronidase, Heparan N-sulfatase, N-Acetyl-α-glucosaminidase, Acetyl CoA-α-glucosaminide N-acetyl transferase, N-acetyl-glucosamine-6 sulfatase, Galactose 6-sulfatase, Arylsulfatase A, B, or C, Arylsulfatase A Cerebroside, Ganglioside, Acid β-galactosidase $G_{M1}$ Gaiglioside, Acid β-galactosidase, Hexosaminidase A, Hexosaminidase B, α-fucosidase, α-N-Acetyl galactosaminidase, Glycoprotein Neuraminidase, Aspartylglucosamine amidase, Acid Lipase, Acid Ceramidase, Lysosomal Sphingomyelinase and other Sphingomyelinase. In certain embodiments, the active agent is dystrophin, components of dystrophin-glycoprotein complex, the laminin-α2 chain, fukutin-related protein, LARGE, fukutin, EMD, LMNA, DMPK, ZNF9, and PABPN1, Glycogen synthase, Glucose-6-phosphatase, Debranching enzyme, Transglucosidase, Myophosphorylase, Phosphorylase, Phosphofructokinase, Acid Maltase Deficiency, Carnitine Palmityl Transferase, Phosphoglycerate Kinase, or Phosphoglycerate Mutase, or a nucleic acid encoding any of said proteins.

In certain embodiments, the substrate is an antibody or fragment thereof. For example, the antibody or fragment thereof may bind nucleosides, nucleotides, nucleobases, oligonucleotides, polynucleotides, or nucleic acid. In certain embodiments in which the substrate is an antibody, it is not the 3E10 antibody or the antibody produced by the hybridoma having the ATCC accession number PTA 2439.

In certain embodiments the substrate portion of the conjugate may be a DNA-binding autoantibody. Examples of such DNA-binding autoantibodies include an antibody having the binding specificity of the antibody as produced by the hybridoma having ATCC accession number PTA 2439, antibody mAb 3E10, and variants and/or functional fragments thereof. The nucleotide and amino acid sequences for the variable region of the heavy chain of mAb 3E10 are provided in FIG. 3. The nucleotide and amino acid sequences for the variable region of the light chains of mAb 3E10 are provided in FIG. 4. In particular, the light chain designated VkIII contains the DNA binding capability for mAb 3E10. Thus, VkIII is the preferred light chain for 3E10 to be used in the methods of the present invention.

Although antibodies that penetrate living cells are frequently toxic or injurious and may explain some of the pathologic manifestations of the autoimmune diseases in which they are found, antibody mAb 3E10, in contrast, shows no harm to cells that it penetrates in tissue culture. Moreover, studies in vitro have shown that mAb 3E10 and scFv fragments of mAb 3E10 can transport relatively large proteins, such as catalase, into the nucleus of cells in tissue culture. Moreover, mAb 3E10 or fragments thereof (e.g., Fv) should not generate significant inflammation in vivo which could hinder therapeutic efficacy of a biologically active molecule conjugated thereto. Monoclonal antibody 3E10 is produced by the hybridoma 3E10 placed permanently on deposit with the American Type Culture Collection, 10801 University Blvd., Manassas, Va. 20110-2209, USA, on Aug. 31, 2000, according to the terms of the Budapest Treaty under ATCC accession number PTA-2439 and are thus maintained and made available according to the terms of the Budapest Treaty. Availability of such strains is not to be construed as a license to practice the invention in contravention of the rights granted under the authority of any government in accordance with its patent laws.

As used herein, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a non-specific antigen (e.g., BSA, casein) other than the predetermined antigen or a closely-related antigen. Alternatively, the antibody can bind with an affinity corresponding to a $K_A$ of about $10^6$ $M^{-1}$, or about $10^7$ $M^{-1}$, or about $10^8$ $M^{-1}$, or $10^9$ $M^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen. In some embodiments the antibody variant or functional fragment will have the same $K_A$ or $K_D$ as an antibody produced by the hybridoma having ATCC accession number PTA 2439. In certain embodiments, the antibody variant or functional fragment will have the same $K_A$ or $K_D$ as mAb 3E10.

The term "$k_d$" ($sec^{-1}$), as used herein, is intended to refer to the dissociation rate constant of a particular antibody-antigen interaction. This value is also referred to as the $k_{off}$ value.

The term "$k_a$" ($M^{-1}$ $sec^{-1}$), as used herein, is intended to refer to the association rate constant of a particular antibody-antigen interaction. The term "$K_A$" (M), as used herein, is intended to refer to the association equilibrium constant of a particular antibody-antigen interaction.

The term "$K_D$" ($M^{-1}$), as used herein, is intended to refer to the dissociation equilibrium constant of a particular antibody-antigen interaction.

Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the "antigen binding" fragments). The third unit, consisting of two equal segments of the heavy chain, is called the Fc fragment. The Fc fragment is typically not involved in antigen-antibody binding, but is important in later processes involved in ridding the body of the antigen.

As used herein, the phrase "functional fragments of an antibody having the binding specificity of the antibody as produced by the hybridoma having ATCC accession number PTA 2439" refers to a fragment that retains the same cell penetration characteristics and binding specificity as mAb 3E10. Thus, in certain embodiments, a functional fragment of an antibody having the binding specificity of the antibody as produced by the hybridoma having ATCC accession number PTA 2439 or antibody mAb 3E10 is used in the conjugate. In some embodiments, the functional fragment used in the conjugate is selected from the group consisting of Fab, F(ab')$_2$, Fv, and single chain Fv (scFv) fragments. In certain embodiments the functional fragment is an Fv fragments or an scFv fragment. In one example, the functional fragment includes at least the antigen-binding portion of mAb 3E10. In another example, the functional fragments is an scFv fragment including the variable region of the heavy chain (VH) and variable region of the kappa light chain (VK) of mAb 3E10. For increased expression in the polynucleotide from which the scFv is expressed, the nucleic acids encoding the chains of mAb E310 are placed in reverse order with the Vκ cDNA being placed 5' of VH. In addition, one or more tags known in the art, preferably peptide (e.g., myc or His$_6$), may be incorporated into a conjugate to facilitate in vitro purification or histological localization of the conjugate. In some embodiments, the a myc tag and a His$_6$ tag are added to the C-terminus of VH.

As readily recognized by those of skill in the art, altered antibodies (e.g., chimeric, humanized, CDR-grafted, bifunctional, antibody polypeptide dimers (i.e., an association of two polypeptide chain components of an antibody, e.g., one arm of an antibody including a heavy chain and a light chain, or an Fab fragment including $V_L$, $V_H$, $C_L$ and $C_H1$ antibody domains, or an Fv fragment comprising a $V_L$ domain and a $V_H$ domain), single chain antibodies (e.g., an scFv (i.e., single chain Fv) fragment including a $V_L$ domain linked to a $V_H$ domain by a linker, and the like) can also be produced by methods well known in the art. Such antibodies can also be produced by hybridoma, chemical synthesis or recombinant methods described, for example, in (Sambrook et al., *Molecular Cloning: A Laboratory Manual* 2d Ed. (Cold Spring Harbor Laboratory, 1989); incorporated herein by reference and Harlow and Lane, *Antibodies: A Laboratory Manual* (Cold Spring Harbor Laboratory 1988), which is incorporated herein by reference). Both anti-peptide and anti-conjugate antibodies can be used (see, for example, Bahouth et al., *Trends Pharmacol. Sci.* 12:338 (1991); Ausubel et al., *Current Protocols in Molecular Biology* (John Wiley and Sons, NY 1989) which are incorporated herein by reference). See in particular, FIGS. 2A, 2B and 3 for specific nucleotide and amino acid sequences of the illustrative antibody of the invention designated mAb 3E10.

For example, antibodies may be humanized by replacing sequences of the Fv variable region which are not directly involved in antigen binding with equivalent sequences from human Fv variable regions. General reviews of humanized chimeric antibodies are provided by Morrison et al., (Science 229:1202-1207, 1985) and by Oi et al. (BioTechniques 4:214, 1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from for example, an antibody producing hybridoma. The recombinant DNA encoding the humanized or chimeric antibody, or fragment thereof, can then be cloned into an appropriate expression vector. Humanized antibodies can alternatively be produced by CDR substitution U.S. Pat. No. 5,225,539; Jones (1986) Nature 321:552-525; Verhoeyan et al. 1988 Science 239: 1534; and Beidler (1988) J. Immunol. 141:4053-4060. Thus, in certain embodiments, the antibody used in the conjugate is a humanized or CDR-grafted form of an antibody produced by the hybridoma having ATCC accession number PTA 2439. In other embodiments the antibody is a humanized or CDR-grafted form of antibody mAb 3E10. For example, the CDR regions of the illustrative antibody of the invention, as shown in FIGS. 2A, 2B and 3, can include amino acid substitutions such as 1, 2, 3, 4, 5, 6, 7, 8, 9, or 10 amino acid differences from those shown in the figures. In some instances, there are anywhere from 1-5 amino acid differences.

As used herein, reference to variants of an antibody having the binding specificity of an antibody as produced by the hybridoma having ATCC accession number PTA 2439" includes variants retaining the same cell penetration characteristics and binding specificity as mAb 3E10, as well as variants modified by mutation to improve the utility thereof (e.g., improved ability to target specific cell types, improved ability to penetrate the cell membrane, improved ability to localize to the cellular DNA, and the like). Such variants include those wherein one or more conservative substitutions are introduced into the heavy chain, the light chain and/or the constant region(s) of the antibody. In some embodiments the variant has a light chain having an amino acid sequence at least 80% or at least 90% or at least 95% identical to the amino acid sequence set forth in SEQ ID NO:8. In other embodiments, the variant has a heavy chain having an amino acid sequence at least 80% or at least 90% or at least 95% identical to the amino acid sequence set forth in SEQ ID NO:6. Further, the invention includes antibodies that are encoded by nucleic acid sequences that hybridize under stringent conditions to the 3E10 variable region coding sequence (e.g., SEQ ID NO:5 and/or SEQ ID NO:7) or encode amino acid sequences at least 80% or at least 90% or at least 95% identical to the amino acid sequence set forth in SEQ ID NO:6 or SEQ ID NO:8.

Such variants include those wherein one or more substitutions are introduced into the heavy chain nucleotide sequence, the light chain nucleotide sequence and/or the constant region(s) of the antibody. In some embodiments the variant has a light chain having a nucleotide sequence at least 80% or at least 90% or at least 95% identical to the nucleotide sequence set forth in SEQ ID NO:7. In other embodiments, the variant has a heavy chain having a nucleotide sequence at least 80% or at least 90% or at least 95% identical to the nucleotide sequence set forth in SEQ ID NO:5.

One exemplary variant contemplated for use in the practice of the present invention is an mAb 3E10 VH variant involving a single change of the aspartic acid residue at position 31 to asparagine (i.e., mAb 3E10-31). The preparation of this variant and further variants and a demonstration of its cell penetration ability is described in U.S. Pat. No. 7,189,396. This particular mAb 3E10 variant is especially well suited for delivery of biological molecules to kidney and brain cells. Other 3E10 variants and/or functional fragments thereof may be used to provide targeting of biologically active molecules. A wide variety of variants and/or functional fragments thereof are possible provided that they exhibit substantially the same cell penetration characteristics as mAb 3E10 or mAb 3E10-31 after conjugation to a selected biologically active molecule.

In other embodiments, novel substrates can be generated that target one or more specific nucleoside transporter. Such novel substrates could be generated using, for example molecular modeling and protein mimetic methodologies based on structures of known substrates.

Conjugates in which the substrate and active agent are polypeptides (i.e., protein conjugates) can be designed to place the active agent at the amino or carboxy terminus the substrate using well-known recombinant DNA methodologies. Such conjugates can be expressed in a host cell as a fusion protein. Alternatively, the substrate and active agent can be chemically linked by a peptide bond or by a chemical or peptide linker molecule of the type well known in the art. The linker may be one or more tags (e.g., myc or $His_6$ (SEQ ID NO:12)) or may be one or more repeats of the known linker sequence GGGGS (SEQ ID NO:11). Additional peptide linkers are known in the art. The skilled artisan will recognize that the linker sequence may be varied depending on the polypeptide to be linked to the antibody.

Vectors suitable for use in preparation of protein conjugates include those selected from baculovirus, phage, plasmid, phagemid, cosmid, fosmid, bacterial artificial chromosome, viral DNA, P1-based artificial chromosome, yeast plasmid, and yeast artificial chromosome. For example, the viral DNA vector can be selected from vaccinia, adenovirus, foul pox virus, pseudorabies and a derivative of SV40. Suitable bacterial vectors for use in practice of the invention methods include pQE70, pQE60, pQE-9, pBLUESCRIPT SK, pBLUESCRIPT KS, pTRC99a, pKK223-3, pDR540, PAC and pRIT2T. Suitable eukaryotic vectors for use in practice of the invention methods include pWLNEO, pXTI, pSG5, pSVK3, pBPV, pMSG, and pSVLSV40. Suitable eukaryotic vectors for use in practice of the invention methods include pWLNEO, pXTI, pSG5, pSVK3, pBPV, pMSG, and pSVLSV40.

Those of skill in the art can select a suitable regulatory region to be included in such a vector, for example from lacI, lacZ, T3, T7, apt, lambda PR, PL, trp, CMV immediate early, HSV thymidine kinase, early and late SV40, retroviral LTR, and mouse metallothionein-I regulatory regions.

Host cells in which the vectors containing the polynucleotides encoding the protein conjugates can be expressed include a bacterial cell, a eukaryotic cell, a yeast cell, an insect cell, or a plant cell. For example, *E. coli, Bacillus, Streptomyces, Pichia pastoris, Salmonella typhimurium, Drosophila* S2, *Spodoptera* SD, CHO, COS (e.g. COS-7), or Bowes melanoma cells are all suitable host cells for use in practice of the invention methods.

Conjugates in which the substrate is a polypeptide and the active agent is a small molecule or drug compound may be generated using methods known in the art. For example, methods for attaching a drug or other small molecule pharmaceutical to protein include bifunctional chemical linkers such as N-succinimidyl (4-iodoacetyl)-aminobenzoate; sulfosuccinimidyl(4-iodoacetyl)-aminobenzoate; 4-succinimidyl-oxycarbonyl-α-(2-pyridyldithio) toluene; sulfosuccinimidyl-6-[α-methyl-α-(pyridyldithiol)-toluamido] hexanoate; N-succinimidyl-3-(-2-pyridyldithio)-proprionate; succinimidyl-6-[3(-(-2-pyridyldithio)-proprionamido]hexanoate; sulfosuccinimidyl-6-[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are disclosed in U.S. Pat. Nos. 5,349,066; 5,618,528; 4,569,789; 4,952,394; and 5,137,877, each of which is incorporated herein by reference in its entirety.

According to a further embodiment of the invention, there are provided methods of screening a conjugate for transport by a nucleoside transport pathway in which the method includes, contacting a cell expressing the nucleoside transport pathway, with a conjugate under suitable conditions for transport to occur; and determining whether the conjugate is transported into the cell by the nucleoside transport pathway. In certain embodiments, the determining step includes comparing the amount of conjugate transported into a cell expressing the nucleoside transport system to the amount of conjugate transported into a control cell not expressing the nucleoside transport system, wherein an increase in transport of conjugate of the cell expressing the nucleoside transport pathway as compared to the control cell indicates transport is by that nucleoside transport pathway.

In particular embodiments of the above screening method, the nucleoside transport pathway includes an equilibrative nucleoside transporter or a concentrative nucleoside transporter. In some embodiments, the equilibrative nucleoside transporter is selected from the group consisting of ENT1, ENT2, ENT3, and ENT4. In certain embodiments, the equilibrative nucleoside transporter is insensitive to low concentrations of nitrobenzylmercaptopurine riboside (NB-MBR). In particular embodiments, the cell is transfected with DNA encoding the nucleoside transporter. Such embodiments may further include a step in which the amount of conjugate transported into the cell transfected with DNA encoding the nucleoside transporter is compared to the amount of conjugate transported into a control cell not transfected with the nucleoside transporter, wherein an increase in transport of conjugate of the transfected cell as compared to the control cell indicates transport is by the nucleoside transporter.

Screening methods may further include compounds that inhibit nucleoside transport activity. For example, NBMPR, dilazep, dipyridamole, and draflazine are inhibitors of certain es nucleoside transporters (e.g., ENT1). Thus, in certain embodiments low concentrations of NBMPR may be included.

In certain embodiments, the conjugate may further contain a detectable label. Such labels are known in the art and include radio-isotopes and fluorescent labels.

Conjugates can be screened directly for their capacity to be transported by nucleoside transport pathways. The screening is typically performed on cells expressing the nucleoside transport pathway. In some methods, the cells are transfected with DNA encoding the a particular nucleoside transporter (NT). In other methods, cells expressing an endogenous NT are used. Cells may express endogenous CNTs and/or an ENTs. In some methods, an ENT is the only NT expressed. In other methods, cells expressing both ENT1 and ENT2 are used.

Internalization of a compound evidencing passage through transporters can be detected by detecting a signal from within a cell from any of a variety of reporters. The reporter can be as simple as a label such as a fluorophore, a chromophore, a radioisotope. Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In some methods, multiple conjugates are screened simultaneously and the identity of each agent or conjugate moiety is tracked using labels linked to the conjugates. In some methods, the screening can be performed in a competition format in which an a conjugate under test and a known substrate of the nucleoside transporter are applied to the same cells. Typically, the conjugate and known substrate are differentially labeled in such assays. Alternatively, the known substrate may be labeled and parallel measurements of uptake of labeled substrate in the presence and absence test conjugate may be compared.

In such comparative assays, the Vmax of a conjugate can be compared with that of known substrate. If a conjugate has a Vmax of at least 1%, preferably at least 5%, more preferably at least 10%, even more preferably at least 20%, and most preferably at least 50% of known substrate for the transporter then the conjugate can be considered to be a substrate for that NT.

Nucleic Acid Therapeutics

In certain embodiments, the compositions herein may be used to deliver nucleic acids, or analogs thereof, to a targeted tissue or cell type. For example, protein expression can be specifically down-regulated using oligonucleotides such, for example, as antisense, locked nucleic acids (LNA), peptide nucleic acids (PNA), morpholino nucleic acids (Morpholinos) and small interfering RNAs (siRNA) of various chemistries. Alternatively, expression constructs may be delivered to cells, to induce expression of a desired gene product.

Nucleic acids which modulate the expression of a certain gene or gene product may be administered. As used herein, "a nucleic acid that modulates expression of . . . " encompasses nucleic acids that up-regulate and down-regulate the expression of the given gene or gene product. For example, an expression construct can expresses the gene of interest and cause up-regulation. Alternatively, a nucleic acid that causes down-regulation can be, for example, a siRNA, a construct that expresses an antisense RNA (such as a short hairpin RNA), or a ribozyme.

Nucleic acid therapeutics, such as oligonucleotides directed against intracellular targets (mRNA or protein), are powerful therapeutic agents. Examples of oligonucleotide therapeutic agents include: antisense oligonucleotides, which are short, single-stranded DNAs and RNAs that bind to complementary mRNA and inhibit translation or induce RNaseH-mediated degradation of the transcript; siRNA oligonucleotides, which are short, double-stranded RNAs that activate the RNA interference (RNAi) pathway leading to mRNA degradation; ribozymes, which are oligonucleotide-based endonucleases that are designed to cleave specific mRNA transcripts; and nucleic acid aptamers and decoys, which are non-naturally occurring oligonucleotides that bind to and block protein targets in a manner analogous to small molecule drugs.

As used herein, the term "nucleic acid" refers to polynucleotides such as deoxyribonucleic acid (DNA), and, where appropriate, ribonucleic acid (RNA). The term should also be understood to include, as appropriate to the context or as applicable to the embodiment being described, both single-stranded polynucleotides (such as antisense) and double-stranded polynucleotides (such as siRNAs). The term "nucleic acid" encompasses, for example, DNA molecules, RNA molecules, RNAi molecules and siRNA molecules, microRNA molecules, native RNA molecules, ribozyme RNA molecules, aptamers, plasmids, cDNA molecules, anti-sense DNA strands, and oligonucleotides. It further encompasses DNA molecules (in the form of plasmids, cDNA, linear DNA, oligos or anti-sense DNA stands) RNA molecules (in the form of siRNA, mRNA, shRNA, ribozymes, RNAi,) aptamers, proteins (antibodies, polypeptides, peptides or fragment of proteins), nucleic acids conjugated to other compounds (such as fluorescent dyes, small molecular inhibitors of specific proteins). There are a number of nucleic acid-based therapeutic agents in various stages of development at this time. Among them are anti-sense agents, aptamers, ribozymes, and small interfering RNAs (siRNAs). M. Faria, H. Ulrich, Curr. Cancer Drug Targets 2002, 2: 355-368.

Antisense agents may be the most advanced class of these agents, with one product (fomivirsen) on the market for the treatment of CMV retinitis, another (alicaforsen) in advanced clinical trials for treatment of Crohn's disease, and Genasense™ (oblimersen sodium), Affinitac™, and Oncomyc-NG™ in clinical trials for treatment of cancer. Antisense agents are typically short, chemically-modified oligonucleotide chains that hybridize to a specific complementary area of a targeted mRNA. The resulting mRNA duplex is recognized and degraded by RNAse H, thereby destroying the mRNA. Because the mRNA instructions fail to reach the ribosome, production of the protein encoded by the targeted mRNA is prevented. By inhibiting the production of proteins involved in disease, antisense drugs can produce a therapeutic benefit.

An aptamer is a DNA or RNA molecule that has been selected from a random or biased pool of oligonucleic acids, based on its ability to bind to a target molecule. Aptamers can be selected which bind nucleic acids, proteins, small organic compounds and specific cell surfaces, and several have been developed which bind to proteins which are associated with disease states. Aptamers are in general more easily manufactured and are more amenable to chemical modification than are antibodies, and they can be "evolved" for tighter binding to the target by an iterative process of random modification and affinity-based selection. The evolved aptamers often have antibody-like specificities, and are therefore expected to have utility in those applications, such as therapeutics and in vitro and in vivo diagnostics, where antibodies have already proved useful. At least one product, Macugen™ (pegaptanib sodium, a PEGylated aptamer with high affinity for VEGF), is in advanced clinical trials for the treatment of age-related macular degeneration.

Ribozymes, or RNA enzymes, are RNA molecules that can catalyze a chemical reaction. All ribozymes found naturally so far catalyze the cleavage of RNA. They range in size from the large "hammerhead" ribozymes to the so-called "minizymes" which are synthetic constructs containing the minimal structures needed for activity. DNA-based enzymes (deoxyribozymes, or DNAzymes) having similar properties have also been prepared. The ability of ribozymes to recognize and cut specific mRNA molecules gives them considerable potential as therapeutic agents. A ribozyme designed to catalyze the cleavage of a specific mRNA would be useful as a therapeutic agent in the same way that a complimentary antisense nucleic acid would be, but with the advantage that a single ribozyme molecule can destroy many copies of the mRNA. A synthetic ribozyme (Angiozyme™) that cleaves the mRNA encoding a VEGF receptor subtype is currently in clinical trials for treatment of cancer.

RNA interference (RNAi) is the phenomenon of gene-specific post-transcriptional silencing by double-stranded RNA oligomers (Elbashir et al. Nature 2001, 411: 494-498; Caplen et al., Proc. Natl. Acad. Sci. U.S.A. 2001, 98: 9742-9747). Small inhibitory RNAs (siRNAs), like antisense oligonucleic acids and ribozymes, have the potential to serve as therapeutic agents by reducing the expression of harmful proteins. The double-stranded siRNA is recognized by a protein complex (the RNA induced silencing complex), which strips away one of the strands, facilitates hybridization of the remaining strand to the target mRNA, and then cleaves the target strand. DNA-based vectors capable of generating siRNA within cells are also of interest for the same reason, as are short hairpin RNAs that are efficiently processed to form siRNAs within cells. siRNAs capable of specifically targeting endogenously and exogenously expressed genes have been described; see for example Paddison et al., Proc. Natl. Acad. Sci. U.S.A., 2002, 99: 1443-1448; Paddison et al., Genes & Dev. 2002, 16: 948-958; Sui et al. Proc. Natl. Acad. Sci. U.S.A. 2002, 8: 5515-5520; and Brummelkamp et al., Science 2002, 296: 550-553.

The term "nucleic acid-based therapeutic agent" as used herein refers to three classes of compounds. The term also includes pharmaceutically acceptable salts, esters, prodrugs, codrugs, and protected forms of the compounds, analogs and derivatives described below. The first class, referred to herein collectively as "antisense nucleic acids," comprises nucleic acids, preferably oligomers of about 50 monomer units or fewer, which have the ability to hybridize in a sequence-specific manner to a targeted single-stranded RNA or DNA molecule. Members of this class include ordinary DNA and RNA oligomers, DNA and RNA having modified backbones, including but not limited to phosphorothioates, phosphorodithioates, methylphosphonates, and peptide nucleic acids, 2'-deoxy derivatives, and nucleic acid oligomers that feature chemically modified purine and pyrimidine bases, or have been lipophilically modified and/or PEGylated to modify their pharmacodynamics. Oligomers that serve as precursors for such agents, such as hairpin RNAs that are converted to siRNAs within cells, are also considered to be within this class.

The second class of nucleic acid-based therapeutic agents is aptamers. Aptamers comprises nucleic acids, preferably oligomers of about 50 monomer units or fewer, which have the ability to bind with structural specificity to a non-oligonucleotide target molecule, or to an oligonucleotide in a manner other than through sequence-specific hybridization. Members of this class include DNA and RNA aptamers, and modifications thereof including but not limited to mirror-image DNA and RNA ("Spiegelmers"), peptide nucleic acids, and nucleic acid oligomers that have otherwise been chemically modified as described above. Again, any of these species may also feature chemically modified purines and pyrimidines or may be lipophilically modified and/or PEGylated. See M. Rimmele, Chembiochem. 2003, 4: 963-71 and A. Vater and S. Klussmann, Curr. Opin. Drug Discov. Devel. 2003, 6: 253-61 for recent reviews of aptamer technology. It will be appreciated that many members of this second class will, in addition to their structure-specific affinity for the target molecule, have sequence-specific affinity for a putative DNA or RNA sequence.

The third class of nucleic acid-based therapeutic agents, referred to herein as "nucleic acid enzymes," comprises nucleic acids that are capable of recognizing and catalyzing the cleavage of target RNA molecules, in a sequence-specific manner. The class includes hammerhead ribozymes, minimized hammerheads ("minizymes"), '10-23' deoxyribozymes ("DNAzymes"), and the like. As with antisense and aptamer molecules, the class includes catalytic species that have been chemically modified.

The term "pharmaceutically acceptable salts" refers to physiologically and pharmaceutically acceptable salts of the compounds of the invention, e.g., salts that retain the desired biological activity of the parent compound and do not impart undesired toxicological effects thereto.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "RNAi construct" is a generic term including siRNA, hairpin RNA, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can be converted into siRNAs in vivo.

As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an episomal vector, e.g., a nucleic acid capable of extra-chromosomal replication. Vectors capable of directing the expression of genes to which they are operatively linked are referred to herein as "expression vectors." In the present specification, "plasmid" and "vector" are used interchangeably unless otherwise clear from the context. In the expression vectors, regulatory elements controlling transcription can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

In one embodiment, the present disclosure relates to the use of antisense nucleic acid to decrease expression of a targeted disease-related protein. Such an antisense nucleic acid can be delivered, for example, as an expression plasmid which, when transcribed in the cell, produces RNA which is complementary to at least a unique portion of the cellular mRNA which encodes the targeted disease-related protein. Alternatively, the construct is an oligonucleotide which is generated ex vivo and which, when introduced into the cell causes inhibition of expression by hybridizing with the mRNA and/or genomic sequences encoding the targeted disease-related protein. Such oligonucleotides are optionally modified so as to be resistant to endogenous exonucleases and/or endonucleases. Exemplary nucleic acid molecules for use as antisense oligonucleotides are phosphoramidate, phosphothioate and methylphosphonate analogs of DNA (see for example U.S. Pat. Nos. 5,176,996; 5,264,564; and 5,256,775). General approaches to constructing oligomers useful in nucleic acid therapy have been reviewed, for example, by van der Krol et al., (1988) Biotechniques 6: 958-976; and Stein et al., (1988) Cancer Res 48: 2659-2668.

In other embodiments, this application relates to the use of RNA interference (RNAi) to effect knockdown of the targeted gene. RNAi constructs comprise double stranded RNA that can specifically block expression of a target gene. RNAi constructs can comprise either long stretches of dsRNA identical or substantially identical to the target nucleic acid sequence, or short stretches of dsRNA identical or substantially identical to only a region of the target nucleic acid sequence.

Optionally, the RNAi constructs may contain a nucleotide sequence that hybridizes under physiologic conditions of the cell to the nucleotide sequence of at least a portion of the mRNA transcript for the gene to be inhibited (the "target" gene). The double-stranded RNA need only be sufficiently similar to natural RNA that it has the ability to induce RNAi. Thus, the invention contemplates embodiments that are tolerant of sequence variations that might be expected due to genetic mutation, polymorphic sites, or evolutionary divergence in a targeted sequence. The number of tolerated nucleotide mismatches between the target sequence and the RNAi construct sequence may be as high as 1 in 5 base pairs, but is preferably no higher than 1 in 10 base pairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Between 90% and 100% sequence identity between the inhibitory RNA and the portion of the target gene is preferred. Alternatively, the duplex region of the RNA may be defined functionally as a nucleotide sequence that is capable of detectably hybridizing with the target gene transcript after hybridization for 12 to 16 hours at 50.degree. C. to 70.degree. C. in 400 mM NaCl, 40 mM PIPES pH 6.4, and 1.0 mM EDTA, followed by washing.

The double-stranded structure may be formed by a single self-complementary RNA strand or two complementary RNA strands. Formation of the dsRNA may be initiated inside or outside of the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications.

The subject RNAi constructs can be "small interfering RNAs" or "siRNAs." These nucleic acids are less than about 50, and preferably around 19-30 nucleotides in length, more preferably 21-23 nucleotides in length. The siRNAs are thought to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme DICER. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art, such as gel electrophoresis. Alternatively, non-denaturing methods, such as column chromatography, size exclusion chromatography, glycerol gradient centrifugation, and affinity purification can be used to purify siRNAs.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one nitrogen or sulfur heteroatom.

Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis. Methods of chemically modifying RNA molecules can be adapted for modifying RNAi constructs (see, e.g., Heidenreich et al. (1997) Nucleic Acids Res. 25: 776-780; Wilson et al. (1994) J. Mol. Recog. 7: 89-98; Chen et al. (1995) Nucleic Acids Res. 23: 2661-2668; Hirschbein et al. (1997) Antisense Nucleic Acid Drug, Dev. 7: 55-61). For example, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted or 2'-deoxy ribonucleosides, .alpha.-configurations, etc.).

In some embodiments, at least one strand of the siRNA molecules may have a 3' overhang from about 1 to about 6 nucleotides in length. Preferably, the 3' overhangs are 1-3 nucleotides in length. In certain embodiments, one strand has a 3' overhang and the other strand is blunt-ended or also has an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine, may be tolerated without reducing the effectiveness of the RNAi. The absence of a 2' hydroxyl significantly enhances the nuclease resistance of the overhang in tissue culture medium, and may be also beneficial in vivo.

The RNAi construct can also be in the form of a long double-stranded RNA, which is digested intracellularly to produce a siRNA sequence within the cell. Alternatively, the RNAi construct may be in the form of a hairpin RNA. It is known in the art that siRNAs can be produced by processing hairpin RNAs in the cell. Hairpin RNAs can be synthesized exogenously or can be formed by transcribing from RNA polymerase III promoters in vivo. Examples of making and using hairpin RNAs for gene silencing in mammalian cells are described in, for example, Paddison et al., Genes Dev, 2002, 16: 948-58; McCaffrey et al., Nature, 2002, 418: 38-9; McManus et al., RNA, 2002, 8: 842-50; Yu et al., Proc. Natl. Acad. Sci. USA, 2002, 99: 6047-52). Preferably, such hairpin RNAs are engineered in cells or in an animal to ensure continuous and stable suppression of a desired gene.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In another embodiment, the present disclosure relates to the use of ribozyme molecules designed to catalytically cleave an mRNA transcript to prevent translation of the mRNA (see, e.g., PCT International Publication WO90/11364, published Oct. 4, 1990; Sarver et al., 1990, Science 247: 1222-1225; and U.S. Pat. No. 5,093,246). While any ribozyme that cleaves the target mRNA at a site-specific recognition sequence can be used to destroy that particular mRNA, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334: 585-591. The ribozymes of the present invention also include RNA endoribonucleases ("Cech-type ribozymes") such as the one which occurs naturally in Tetrahymena thermophila (known as the IVS or L-19 IVS RNA) and which has been extensively described (see, e.g., Zaug, et al., 1984, Science, 224: 574-578; Zaug and Cech, 1986, Science, 231: 470-475; Zaug, et al., 1986, Nature, 324: 429-433; published International patent application No. WO88/04300 by University Patents Inc.; Been and Cech, 1986, Cell, 47: 207-216).

In a further embodiment, the invention relates to the use of DNA enzymes to inhibit expression of a targeted gene. DNA enzymes incorporate some of the mechanistic features of both antisense and ribozyme technologies. DNA enzymes are designed so that they recognize a particular target nucleic acid sequence, much like an antisense oligonucleotide; however, much like a ribozyme, they are catalytic and specifically cleave the target nucleic acid. Briefly, to design an ideal DNA enzyme that specifically recognizes and cleaves a target nucleic acid, one of skill in the art must first identify a unique (or nearly unique) target sequence. Preferably, the sequence is a G/C rich stretch of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

The methods described herein may be used to deliver a variety of molecules, including but not limited to small molecules (including small molecules that do not have optimal cell-permeability), lipids, nucleosides, nucleotides, nucleic acids, polynucleotides, oligonucleotides, antibodies, toxins, negatively charged polymers and other polymers, for example proteins, peptides, hormones, carbohydrates, or polyamines, across cellular membranes. Non-limiting examples of polynucleotides that can be delivered across cellular membranes using the compounds and methods of the invention include short interfering nucleic acid (siNA), antisense, enzymatic nucleic acid molecules, 2',5'-oligoadenylate, triplex forming oligonucleotides, aptamers, and decoys. Biologically active molecules that may be delivered include antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, allozymes, aptamers, decoys and analogs thereof, and small nucleic acid molecules, such as short interfering nucleic acid (siNA), short interfering RNA (siRNA), double-stranded RNA (dsRNA), micro-RNA (miRNA), antagomirs, and short hairpin RNA (shRNA) molecules, to relevant cells and/or tissues, such as in a subject or organism.

The compounds, compositions, and methods of the invention can increase delivery or availability of biologically active molecules (e.g., siNAs, siRNAs, miRNAs, siRNA and miRNA inhibitors, nucleic acids, polynucleotides, oligonucleotides, peptides, polypeptides, proteins, hormones, antibodies, and small molecules) to cells or tissues compared to delivery of the molecules in the absence of the compounds, compositions, and methods of the invention. As such, the level of a biologically active molecule inside a cell, tissue, or organism is increased in the presence of the compounds and compositions of the invention compared to when the compounds and compositions of the invention are absent.

The term "ligand" refers to any compound or molecule, such as a drug, peptide, hormone, or neurotransmitter that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association. Non-limiting examples of ligands include sugars and carbohydrates such as galactose, galactosamine, and N-acetyl galactosamine; hormones such as estrogen, testosterone, progesterone, glucocortisone, adrenaline, insulin, glucagon, cortisol, vitamin D, thyroid hormone, retinoic acid, and growth hormones; growth factors such as VEGF, EGF, NGF, and PDGF; cholesterol; bile acids; neurotransmitters such as GABA, Glutamate, acetylcholine; NOGO; inostitol triphosphate; diacylglycerol; epinephrine; norepinephrine; Nitric Oxide, peptides, vitamins such as folate and pyridoxine, drugs, antibodies and any other molecule that can interact with a receptor in vivo or in vitro. The ligand can be attached to a compound of the invention using a linker molecule, such as an amide, amido, carbonyl, ester, peptide, disulphide, silane, nucleoside, abasic nucleoside, polyether, polyamine, polyamide, peptide, carbohydrate, lipid, polyhydrocarbon, phosphate ester, phosphoramidate, thiophosphate, alkylphosphate, or photolabile linker. In one embodiment, the linker is a biodegradable linker.

Linkers

A variety of linkers may be used to link the substrate capable of being transported to the active agent. For example, degradable and cleavable linkers may be used.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage. The term "photolabile linker" as used herein, refers to linker moieties as are known in the art that are selectively cleaved under particular UV wavelengths. Compounds of the invention containing photolabile linkers can be used to deliver compounds to a target cell or tissue of interest, and can be subsequently released in the presence of a UV source.

The term "linker" as used herein is any bond, small molecule, or other vehicle which allows the substrate and the active agent to be targeted to the same area, tissue, or cell. In certain embodiments, the linker is cleavable.

In one embodiment the linker is a chemical bond between one or more substrates and one or more therapeutic moieties. Thus, the bond may be covalent or ionic. An example of a therapeutic complex where the linker is a chemical bond would be a fusion protein. In one embodiment, the chemical bond is acid sensitive and the pH sensitive bond is cleaved upon going from the blood stream (pH 7.5) to the transcytotic vesicle or the interior of the cell (pH about 6.0). Alternatively, the bond may not be acid sensitive, but may be cleavable by a specific enzyme or chemical which is subsequently added or naturally found in the microenvironment of the targeted site. Alternatively, the bond may be a bond that is cleaved under reducing conditions, for example a disulfide bond.

Alternatively, the bond may not be cleavable.

Any kind of acid cleavable or acid sensitive linker may be used. Examples of acid cleavable bonds include, but are not limited to: a class of organic acids known as cipolycarboxylic alkenes. This class of molecule contains at least three carboxylic acid groups (COOH) attached to a carbon chain that contains at least one double bond. These molecules as well as how they are made and used is disclosed in Shen, et al. U.S. Pat. No. 4,631,190.

Alternatively, molecules such as amino-sulfhydryl crosslinking reagents which are cleavable under mildly acidic conditions may be used. These molecules are disclosed in Blattler et al., U.S. Pat. No. 4,569,789.

Alternatively, the acid cleavable linker may be a time-release bond, such as a biodegradable, hydrolyzable bond. Typical biodegradable carrier bonds include esters, amides or urethane bonds, so that typical carriers are polyesters, polyamides, polyurethanes and other condensation polymers having a molecular weight between about 5,000 and 1,000,000. Examples of these carriers/bonds are shown in Peterson, et al., U.S. Pat. No. 4,356,166. Other acid cleavable linkers may be found in U.S. Pat. Nos. 4,569,789 and 4,631,190 or Blattner et al. in Biochemistry 24: 1517-1524 (1984). The linkers are cleaved by natural acidic conditions, or alternatively, acid conditions can be induced at a target site as explained in Abrams et al., U.S. Pat. No. 4,171,563.

Examples of linking reagents which contain cleavable disulfide bonds (reducible bonds) include, but are not limited to"DPDPB", 1,4-di-[3'-(2'-pyridyldithio) propionamido]butane; "SADP", (N-succinimidyl (4-azidophenyl) 1,3'-dithiopropionate); "Sulfo-SADP" (Sulfosuccinimidyl (4-azidophenyldithio) propionate; "DSP"-Dithio bis(succinimidylproprionate); "DTSSP"-3,3'-Dithio bis(sulfosuccinimidylpropionate); "DTBP"-dimethyl 3,3dithiobispropionimidate-2 HCl, all available from Pierce Chemicals (Rockford, Ill.).

Examples of linking reagents cleavable by oxidation are"DST"-disuccinimidyl tartarate; and"Sulfo-DST"-disuccinimidyl tartarate. Again, these linkers are available from PierceChemicals.

Examples of non-cleavable linkers are"Sulfo-LC-SMPT"-(sulfosuccinimidyl 6-[alphamethyl-alpha-(2-pyridylthio) toluamido}hexanoate; "SMPT"; "ABH"-Azidobenzoyl hydrazide; "NHS-ASA"-N-Hydroxysuccinimidyl-4-azidosalicyclic acid; "SASD"-Sulfosuccinimidyl 2-(pazidosalicylamido)ethyl-1,3-dithiopropionate; "APDP"-N-{4-(p-azidosalicylamido) buthy}-3' (2'-pyidyldithio) propionamide; "BASED"-Bis-[beta-(4-azidosalicylamido)ethyl]disulfide; "HSAB"-N-hydroxysuccinimidyl-4 azidobenzoate; "APG"-p-Azidophenyl glyoxal monohydrate; "SANPAH"-N-Succiminidyl-6 (4'-azido-2'-mitrophenyl-amimo) hexanoate; "Sulfo-SANPAH"-Sulfosuccinimidyl6-(4'-azido-2'-nitrophenylamino) hexanoate; "ANB-NOS" N-5-Azido-2-nitrobenzoyloxysuccinimide; "SAND"-Sulfosuccinimidyl-2-(m-azido-o-mitrobenzamido)-ethyl-1, 3'-dithiopropionate; "PNP-DTP"-p-nitrophenyl-2-diazo-3,3, 3trifluoropropionate; "SMCC"-Succinimidyl4-(N-maleimidomethyl)cyclohexane-1-carboxylate; "Sulfo-SMCC"-Sulfosuccinimidyl4-(N-maleimidomethyl) cyclohexane-1-carboxylate; "MBS" m-Maleimidobenzoyl-N-hydroxysuccinimide ester; "sulfo-MBS"-m-

Maleimidobenzoyl-N-hydroxysulfosuccinimide ester; "SIAB"-N-Succinimidyl (4-iodoacetyl)aminobenzoate; "SulfSIAB"-N-Sulfosuccinimidyl (4-iodoacetyl)aminobenzoate; "SMPB"-Succinimidyl 4-(pmaleimidophenyl) butyrate; "Sulfo-SMPB"-Sulfosuccinimidyl 4-(p-malenimidophenyl) butyrate; "DSS"-Disuccinimidyl suberate; "BSSS"-bis(sulfosuccinimidyl) suberate; "BMH"-Bis maleimidohexane; "DFDNB"-1,5-difluoro-2,4-dinitrobenzene; "DMA"-dimethyl adipimidate 2 HCI; "DMP"-Dimethyl pimelimidate-2HCI; "DMS"-dimethyl suberimidate-2-HCI; "SPDPN-succinimidyl-3-(2-pyridylthio) propionate;" Sulfo-HSAB"-Sulfosuccinimidyl 4-(pazidophenyl) butyrate; "Sulfo-SAPB"-Sulfosuccinimidyl 4-(p-azidophenylbutyrate); "ASIB"-1-9p-azidosalicylamido)-4-(iodoacetamido) butane; "ASBA"-4-(p-Azidosalicylamido)butylamine. All of these linkers are available from Pierce Chemicals.

In another embodiment the linker is a small molecule such as a peptide linker. In one embodiment the peptide linker is not cleavable. In a further embodiment the peptide linker is cleavable by base, under reducing conditions, or by a specific enzyme. In one embodiment, the enzyme is indigenous. Alternatively, the small peptide may be cleavable by an non-indigenous enzyme which is administered after or in addition to the therapeutic complex. Alternatively, the small peptide may be cleaved under reducing conditions, for example, when the peptide contains a disulfide bond. Alternatively, the small peptide may be pH sensitive. Examples of peptide linkers include: poly(L-Gly), (Poly L-Glycine linkers); poly(L-Glu), (PolyL-Glutamine linkers); poly (L-Lys), (Poly L-Lysine linkers). In one embodiment, the peptide linker has the formula (amino acid) n, where n is an integer between 2 and 100, preferably wherein the peptide comprises a polymer of one or more amino acids.

In a further embodiment, the peptide linker is cleavable by proteinase such as one having the sequence Gly-(D) Phe-Pro-Arg-Gly-Phe-Pro-Ala-Gly-Gly (SEQ ID NO:13) (Suzuki, et al. 1998, J. Biomed. Mater. Res. October; 42 (1): 112-6). This embodiment has been shown to be advantageous for the treatment of bacterial infections, particularly *Pseudomonas aeruginosa*. Gentamicin or an alternate antibiotic is cleaved only when the wounds are infected by *Pseudomonas aeruginosa* because there is significantly higher activity of thrombin-like proteinase enzymes then in noninfected tissue.

In a further embodiment the linker is a cleavable linker including, poly (ethylene glycol) (PEG) and a dipeptide, L-alanyl-L-valine (Ala-Val), cleavable by the enzyme thermolysin. This linker is advantageous because thermolysin-like enzyme has been reported to be expressed at the site of many tumors. Alternatively, a 12 residue spacer Thr-Arg-His-Arg-Gln-Pro-Arg-Gly-Trp-Glu-Gln-Leu (SEQ ID NO: 14) may be used which contains the recognition site for the protease furin (Goyal, et al. Biochem. J. 2000 Jan. 15; 345 Pt 2: 247-254).

The chemical and peptide linkers can be bonded between the substrate and the active agent by techniques known in the art for conjugate synthesis, i.e. using genetic engineering, or chemically. The conjugate synthesis can be accomplished chemically via the appropriate antibody by classical coupling reactions of proteins to other moieties at appropriate functional groups.

Examples of the functional groups present in proteins and utilized normally for chemical coupling reactions are outlined as follows. The carbohydrate structures may be oxidized to aldehyde groups that in turn are reacted with a compound containing the group H2NNH—R (wherein R is the compound) to the formation of aC=NH—NH—R group. The thiol group (cysteines in proteins) may be reacted with a compound containing a thiol-reactive group to the formation of a thioether group or disulfide group. The free amino group (at the amino terminus of a protein or on a lysine) in amino acid residues may be reacted with a compound containing an electrophilic group, such as an activated carboxy group, to the formation of an amide group. Free carboxy groups in amino acid residues may be transformed to a reactive carboxy group and then reacted with a compound containing an amino group to the formation of an amide group.

The linker may alternatively be a liposome. Many methods for the preparation of liposomes are well known in the art. For example, the reverse phase evaporation method, freeze thaw methods, extrusion methods, and dehydration-rehydration methods. (see Storm, et al. PSTT 1: 19-31 (1998),).

The liposomes may be produced in a solution containing the active agent so that the substance is encapsulated during polymerization. Alternatively, the liposomes can be polymerized first, and the biologically active substance can be added later by resuspending the polymerized liposomes in a solution of a biologically active substance and treating with sonication to affect encapsulation of the active agent. The liposomes can be polymerized in the presence of the substrate such that the substrate becomes a part of the phospholipid bilayer. In one embodiment, the liposome contains the active agent on the inside and the substrate on the outside.

The liposomes contemplated in the present invention can comprise a variety of structures. For example, the liposomes can be multilamellar large vesicles (MLV), oligolamellar vesicles (OLV), unilamellar vesicles (UV), small unilamellar vesicles (SUV), medium sized unilamellar vesicles (MUV), large unilamellar vesicles (LUV), giant unilamellar vesicles (GUV), or multivesicular vesicles (MVV). Each of these liposome structures are well known in the art (see Storm, et al. PSTT 1: 19-31 (1998)).

In one embodiment, the liposome is a "micromachine" that evulses pharmaceuticals for example by the application of specific frequency radio waves. In another embodiment, the liposomes can be degraded such that they will release the active agent in the targeted cell, for example, the liposomes may be acid or alkaline, sensitive, or degraded in the presence of a low or high pH, such that the active agent is released within the cell. Alternatively, the liposomes may be uncharged so that they will be taken up by the targeted cell. The liposomes may also be pH sensitive or sensitive to reducing conditions.

One type of liposome which may be advantageously used in the present invention is that identified in Langer et al., U.S. Pat. No. 6,004,534, issued Dec. 21, 1999. In this application a method of producing modified liposomes which are prepared by polymerization of double and triple bond-containing monomeric phospholipids is disclosed. These liposomes have surprisingly enhanced stability against the harsh environment of the gastrointestinal tract. Thus, they have utility for oral and/or mucosal delivery of the active agent. It has also been shown that the liposomes may be absorbed into the systemic circulation and lymphatic circulation. The liposomes are generally prepared by polymerization (i.e., radical initiation or radiation) of double and triple bond-containing monomeric phospholipids.

In other embodiments of the present invention, the linker can also be a liposome having a long blood circulation time. Such liposomes are well known in the art, (see U.S. Pat. Nos. 5,013,556; 5,225,212; 5,213,804; 5,356,633; and 5,843, 473). Liposomes having long blood circulation time are characterized by having a portion of their phospholipids derivatized with polyethylene glycol (PEG) or other similar polymer. In some embodiments, the end of the PEG molecule distal to the phospholipid may be activated so a to be chemically reactive. Such a reactive PEG molecule can be used to link a substrate to the liposome. One example of a reactive PEG molecule is the maleimide derivative of PEG described in U.S. Pat. No. 5,527,528).

Alternatively, the linker may be a microcapsule, a nanoparticle, a magnetic particle, and the like (Kumar, J. Pharm. Sci., May-August 3 (2) 234-258, 2000; and Gill et al., Trends Biotechnol. November; 18(11): 469-79, 2000), with the lipophilic active agent on or in the container, and the container functioning as the linker in the therapeutic complex.

Alternatively, the linker may be a photocleavable linker. For example, a 1-2-(nitrophenyl)ethyl moiety can be cleaved using 300 to 360 nm light (see Pierce catalog no. 21332ZZ). It can be envisioned that the photocleavable linker would allow activation and action of the drug in an even more specific area, for example a particular part of the organ. The light could be localized using a catheter into the vessel. Alternatively, light may be used to localize treatment to a specific part of the digestive tract and the light may be manipulated through a natural orifice to the area.

Alternatively, the light can be surgically manipulated to the area.

Alternatively, the linker may not be cleavable, but the active agent or substrate is. An example of this is when the active agent is a prodrug and the enzyme which cleaves the prodrug is administered with the therapeutic complex. Alternatively, the enzyme is part of the therapeutic complex or indigenous and the prodrug is administered separately. Preferably, the enzyme or prodrug which is administered separately is administered within about 48 hours of the first administration. Alternatively, the prodrug or enzyme which is administered separately may be administered between about 1 min and 24 hours, alternatively between about 2 min and 8 hours.

The prodrug or enzyme which is administered separately, may be readministered at a later date and may continue to be administered until the effect of the drug is not longer needed.

According to yet another embodiment of the invention, there are provided methods for treating a disease or disorder in a cell or tissue expressing a nucleoside transport pathway. The method includes administering to a patient having the disease or disorder a conjugate including a substrate that is capable of being transported by the nucleoside transport pathway expressed in the affected cell or tissue and an active agent for treating disease or disorder, wherein the conjugate is also transported by the nucleoside transport pathway. In this way, the conjugate is transported into the affected cells or tissue, thereby delivering the active agent.

Diseases or disorders which may be treated using a conjugate of the invention include diseases or disorders involving tissues such as muscle (including skeletal muscle and cardiac muscle), glycogen-storing cells, vascular endothelium, heart, brain, placenta, thymus, pancreas, prostate, kidney, blood, skin, and ENT2-expressing cancer cells.

In certain embodiments the disease or disorder involves muscle such as skeletal or cardiac muscle and the conjugate is transported into the muscle cells (such as skeletal muscle cells or cardiac muscle cells), thereby delivering the active agent. In certain embodiments, the muscle disorder is selected from the group consisting of cachexia, muscle dystrophies, lysosomal muscle disorders, skeletal muscle disorders, smooth muscle disorders, and cardiac muscle disorders. In certain embodiments, these designations may overlap. Muscle dystrophies include Becker's muscular dystrophy (BMD), Congenital muscular dystrophy, Duchenne muscular dystrophy (DMD), Distal muscular dystrophy, Emery-Dreifuss muscular dystrophy, Facioscapulohumeral muscular dystrophy (FSHD), Limb-girdle muscular dystrophy (LGMD), Myotonic muscular dystrophy, and Oculopharyngeal muscular dystrophy. In certain embodiments, a lysosomal disorder is Pompe Disease, Hurler Syndrome, Fabry Disease, Maroteaux-Lamy Syndrome, Morquio Syndrome, Hunter Syndrome, Farber Disease, Krabbe Disease, Sly Syndrome, Sanfilippo (including A, B, and D), Morquio A, Multiple Sulfatase Deficiency, Metachromatic Leukodystrophy, Mucolipidosis IV, G.sub.MI Gangliosidosis, Galactosialidosis, Tay-Sachs and Tay-Sachs Variants, Sandhoff, Fucsidosis, Schindler Disease, Sialidosis, Aspartylglucosaminuria, Wolman Disease, Farber Lipogranulomatosis, and Nieman-Pick disease. In certain embodiments, the cardiac muscle disorder is cardiomyopathy, cardiac ischemia, congestive heart failure, ischemia-reperfusion injury, Coronary heart disease, Cardiovascular disease, schaemic heart disease, Heart failure, Hypertensive heart disease, Inflammatory heart disease, and Valvular heart disease. The muscle disorder may be sarcopenia. In some embodiments, the muscle disorder is muscle wasting caused by another disease, such as AIDS or cancer. Other muscle disorders include diseases of the neuromuscular junction, such as myasthenia gravis, Lambert-Eaton syndrome, and Congenital Myasthenic Syndrome, motor neuron diseases (such as ALS, spinal muscular atrophy, Charcot-Maria-Tooth disease, and Freidrich's Ataxia), inflammatory myopathies (such as dermatomyositis, polymyositis, and inclusion body myositis), endocrine abnormalities (such as hyperthyroid myopathy), myotonia, nemaline myopathy, and myotubular myopathy. Enzyme deficiency disorders of the muscles include Phosphorylase Deficiency, Acid Maltase Deficiency, Mitochondrial Myopathy, Carnitine Palmityl Transferase Deficiency, Phosphoglycerate Kinase Deficiency, and Phosphoglycerate Mutase Deficiency.

In particular embodiments, the active agent effective in the treatment of a skeletal muscle disorder may be, for example, an enzyme that is lacking in a patient with the muscle disorder. For example, the following skeletal muscle diseases and disorders may be treated with the following enzymes, or a nucleic acid that modulates the expression of said enzymes, in accordance with the methods herein: α-glucosidase (Pompe Disease), α-L-iduronidase (Hurler Syndrome), α-galactosidase A (Fabry Disease), arylsulfatase (Maroteaux-Lamy Syndrome), N-acetylgalactosamine-6-sulfatase or β-galactosidase (Morquio Syndrome), iduronate 2-sulfatase (Hunter Syndrome), ceramidase (Farber Disease), galactocerebrosidase (Krabbe Disease), β-glucuronidase (Sly Syndrome), Heparan N-sulfatase (Sanfilippo A), N-Acetyl-α-glucosaminidase (Sanfilippo B), Acetyl CoA-α-glucosaminide N-acetyl transferase, N-acetyl-glucosamine-6 sulfatase (Sanfilippo D), Galactose 6-sulfatase (Morquio A), Arylsulfatase A, B, and C (Multiple Sulfatase Deficiency), Arylsulfatase A Cerebroside (Metachromatic Leukodystrophy), Ganglioside (Mucolipidosis IV), Acid β-galactosidase G.sub.MI Gaiglioside (G.sub.MI Gangliosidosis), Acid β-galactosidase (Galactosialidosis), Hexosaminidase A (Tay-Sachs and Variants), Hexosaminidase B (Sandhoff), α-fucosidase (Fucsidosis), α-N-Acetyl galactosaminidase (Schindler Disease), Glycoprotein Neuraminidase (Sialidosis), Aspartylglucosamine amidase (Aspartylglucosaminuria), Acid Lipase (Wolman Disease), Acid Ceramidase (Farber Lipogranulomatosis), Lysosomal Sphingomyelinase and other Sphingomyelinase (Nieman-Pick). In certain embodiments, the active agent is dystrophin, components of dystrophin-glycoprotein complex, the laminin-α2 chain, fukutin-related protein, LARGE, fukutin, EMD, LMNA, DMPK, ZNF9, and PABPN1, or a nucleic acid that modulates the expression of said proteins.

In certain embodiments the disease or disorder involves glycogen-storing cells and the conjugate is transported into the glycogen-storing cells, thereby delivering the active agent. Glycogen-storing cells include muscle cells, liver cells, and also kidney and intestinal cells. In certain embodiments, the glycogen-storage disorder is selected from the group consisting of Glycogen synthase deficiency, Glucose-6-phosphatase deficiency (von Gierke disease), Debranching enzyme deficiency (Forbes-Cori disease), Transglucosidase deficiency, (Andersen disease, amylopectinosis), Myophosphorylase deficiency (McArdle disease), Phosphorylase deficiency (Hers disease), and Phosphofructokinase deficiency (Tauri disease). In particular embodiments, the active agent effective in the treatment of a glycogen-storage disorder is Glycogen synthase, Glucose-6-phosphatase, Debranching enzyme, Transglucosidase, Myophosphorylase, Phosphorylase, Phosphofructokinase, Acid Maltase Deficiency, Carnitine Palmityl Transferase, Phosphoglycerate Kinase, or Phosphoglycerate Mutase, or a nucleic acid that up-regulates the expression of the deficient proteins.

In certain embodiments the disease or disorder involves vascular endothelium and the conjugate is transported into the vascular endothelium, thereby delivering the active agent. In certain embodiments, the vascular endothelium disorder is selected from the group consisting of inappropriate angiogenesis (for example, surrounding a tumor), deficient angiogenesis (for example, in a slowly-healing wound or ulcer), restenosis, atherosclerosis, scarring after surgery or injury, and vasculitis. Examples of diseases associated with uncontrolled angiogenesis that may be treated with the compositions and methods herein include, but are not limited to retinal/choroidal neovascularization and corneal neovascularization. Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma. Example of deficient angiogenesis include ulcers such as skin ulcers and diabetic ulcers. In one embodiment, the active agent effective in the treatment of a disease of the vascular endothelium is serum amyloid P (SAP), or a nucleic acid that increases SAP expression. SAP inhibits fibrocytes from causing pathological scarring lesions. In another embodiment, the disease of the vascular endothelium is atherosclerosis, which may be treated using statins, niacin, intestinal cholesterol absorption-inhibiting supplements such as ezetimibe and fibrates, aspirin, human Apo-A1 Milano HDL, or a nucleic acid that increases Apo-A1 Milano HDL expression. One may also administer nucleic acids that reduce synthesis of cholesterol, such as siRNA constructs designed to reduce expression of cholesterol synthetic enzymes. Cholesterol synthetic enzymes include HMG-CoA synthase, HMG-CoA reductase, mevalonate kinase, phosphomevalonate kinase, and lanosterol synthase.

In certain embodiments the disease or disorder involves the brain and the conjugate is transported into the brain cells, thereby delivering the active agent. In certain embodiments, the brain disorder is selected from the group consisting of neurodegenerative diseases (such as Alzheimer's disease, Parkinson's disease, motor neuron disease, and Huntington's disease), mental illnesses, such as clinical depression, schizophrenia, bipolar disorder, and post-traumatic stress disorder; infectious diseases including meningitis, viral, bacterial, and prion diseases, inherited disorders such as Tay-Sachs disease, Fragile X syndrome, and Down syndrome, and lysosomal storage disorders. In particular embodiments, the active agent effective in the treatment of a disease of the brain is an enzyme absent (or present at reduced levels) in a patient with a lysosomal storage disorder; examples of lysosomal disorders, and compositions for treating them, are listed above.

In certain embodiments the disease or disorder involves the placenta and the conjugate is transported into the placental cells, thereby delivering the active agent. In certain embodiments, the placental disorder is selected from the group consisting of Placenta accreta, Placenta praevia, and Placental abruption.

In certain embodiments the disease or disorder involves the thymus and the conjugate is transported into cells of the thymus, thereby delivering the active agent. In certain embodiments, the thymus disorder is selected from the group consisting of an autoimmune disease, a disease resulting from faulty positive selection or faulty negative selection of T cells, and cancer of the thymus. Some examples of autoimmune diseases include Alopecia Areata, Ankylosing Spondylitis, Antiphospholipid Syndrome, Autoimmune Addison's Disease, Autoimmune Hemolytic Anemia, Autoimmune Hepatitis, Behçet's Disease, Bullous Pemphigoid, Cardiomyopathy, Celiac Sprue-Dermatitis, Chronic Fatigue Immune Dysfunction Syndrome (CFIDS), Chronic Inflammatory Demyclinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barr, Hashimoto's Thyroiditis, Hypothyroidism, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Meniere's Disease, Mixed Connective Tissue Disease, Multiple Sclerosis, Myasthenia Gravis, *Pemphigus Vulgaris*, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and myasthenia gravis. In particular embodiments, the active agent effective in the treatment of a disease of the thymus is immunosuppressive or anti-inflammatory. The agent may be, for example, an antibody including muromab, basiliximab, and daclizumab, or a nucleic acid encoding one of those antibodies. Examples of immunosuppressive and anti-inflammatory drugs that may be used as the active agent include corticosteroids, rolipram, calphostin, CSAIDs; interleukin-10, glucocorticoids, salicylates, nitric oxide; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-.alpha inhibitors such as tenidap, anti-TNF antibodies or soluble TNF receptor, and rapamycin (sirolimus or Rapamune) or derivatives thereof. When the disease is cancer of the thymus, the active agent may be a chemotherapeutic drug or other type of anti-cancer therapeutic.

In certain embodiments the disease or disorder involves the pancreas and the conjugate is transported into cells of the pancreas, thereby delivering the active agent. In certain embodiments, the pancreas disorder is selected from the group consisting of Pancreatitis, Diabetes mellitus, Exocrine pancreatic insufficiency, complications of Cystic fibrosis, Pseudocysts, or pancreatic cancer. In particular embodiments, the active agent effective in the treatment of a disease of the pancreas is insulin, a Pancreatic Enzyme Product (PEP) such as pancrelipase, or a nucleic acid that up-regulates expression of the same.

In certain embodiments the disease or disorder involves the prostate and the conjugate is transported into cells of the prostate, thereby delivering the active agent. In certain embodiments, the prostate disorder is selected from the group consisting of Prostatitis, Benign prostatic hyperplasia, or Prostate cancer. In particular embodiments, the active agent effective in the treatment of a disease of the prostate is an anti-cancer agent; examples of such agents are listed elsewhere in this application.

In certain embodiments the disease or disorder involves the kidney and the conjugate is transported into cells of the kidney, thereby delivering the active agent. In certain embodiments, the kidney disorder is selected from the group consisting of Diabetic nephropathy, Glomerulonephritis, Hydronephrosis, Kidney stones, Kidney tumors (such as Wilms tumor and Renal cell carcinoma), Lupus nephritis, Minimal change disease, Pyelonephritis, nephrotic syndrome, and Renal failure (such as Acute renal failure and Stage 5 Chronic Kidney Disease). In particular embodiments, the active agent effective in the treatment of a disease of the kidney is an agent that treats autoimmune disease, or an anti-cancer therapeutic, both of which are listed elsewhere in the present application.

In certain embodiments the disease or disorder involves the blood and the conjugate is transported into cells of the blood, thereby delivering the active agent. In certain embodiments, the blood disorder is selected from the group consisting of: primary immunodeficiency (including SCID, hemophilia A, and hemophilia B), reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, bone marrow disorders caused by radiation, chemical or chemotherapeutic induced bone marrow aplasia or myelosuppression, acquired immune deficiency syndrome, and polycythemia rubra vera. In particular embodiments, the active agent effective in the treatment of a disease of the blood is selected from the group consisting of corticosteroids, anti-leukemic agents, growth factors, and clotting factors. In certain embodiments, the clotting factor is Factor VIII or IX. In certain aspects, SCID is caused by a recessive mutation and may be treated by administering a wild-type copy of the missing protein (or a nucleic acid encoding that protein). For example, X-linked SCID may be treated with IL2RG, Jak3 gene mutations may be treated with JAK3, ADA gene mutations may be treated with ADA, IL-7R alpha-chain mutations may be treated with IL7R alpha, CD3 delta or epsilon mutations may be treated with CD3 delta or epsilon, RAG1/RAG2 mutations may be treated with RAG1/RAG2, Artemis gene mutations may be treated with ARTEMIS, and CD45 gene mutations may be treated with CD45. Other types of primary immunodeficiency are deficiencies in the following proteins: DNA ligase type I, CD40 ligand, CD40, Purine nucleoside phosphorylase (PNP), MHC class II, CD3γ, CD8, ZAP-70, TAP-1/2, Winged helix protein, CD19, TACI, BAFF receptor, AICDA, uracil-DNA glycosylase, perforin, MUNC13D, syntaxin 11, CD95, Fas ligand, CASP8, and CASP10. These deficiencies may be treated by administration of the deficient protein or a nucleic acid encoding it.

In certain embodiments the disease or disorder involves the skin and the conjugate is transported into cells of the skin, thereby delivering the active agent. In certain embodiments, the skin disorder is selected from the group consisting of dermatomyositis, papulosquamous dermatoses, bacterial dermatoses, viral dermatoses, mycolic skin infections, granulomatous dermatoses, parasitic skin dermatoses, exfoliative dermatitis, bullous dermatoses, pigmented dermatoses, photosensitive dermatoses, dermatoses caused by collagen diseases, dermatoses due to internal diseases, xerosis, urticaria, atopic dermatitis, eczyma, lichen simplex chronicus, psoriasis, scabies, wound, sun burn, cold sores, acne, insect bite, radiotherapy or chemotherapy-induced dermatitis, paraneoplastic syndrome, malignancy, melanoma, primary skin cancer, and metastatic skin cancer. In particular embodiments, the active agent effective in the treatment of a disease of the skin is anthralin, calpotriene, coal tar, diclofenac, T4 endonuclease, isotretinoin, acitretin, cidofoir, a corticosteroid, an antibiotic, an analgesic, an immunomodulator, including oral immunomodulator such as tacrolimus and pimecrolimus, and topical immunomodulators; an immunosuppressant, an anti-angiogenic, including anti-VEGF, anti-FGF, anti-EGF and anti-HGF; a leukotriene modifier, an aminosalicylate, an anesthetic, a non-steroidal anti-inflammatory, a modifier of a solubilized interleukin receptor, an inhibitor of a tyrosine-kinase receptor, a protein kinase C inhibitor, methotrexate, cyclosporine, and methylprednisolone acetate.

In certain embodiments the disease or disorder is a type of cancer and the conjugate is transported into cancer cells, thereby delivering the active agent. In certain embodiments, the type of cancer is selected from the group consisting of rhabdomyosarcoma, ovarian cancer, colon cancer, and breast cancer. In other embodiments, the cancer is selected from leukemia, lymphomas, melanomas, squamous cell carcinomas, breast cancer, prostate cancer, bladder cancer, lung cancer including non small-cell lung cancer and small-cell lung cancer, ovarian cancer, colon cancer, squamous cell carcinoma, astrocytoma, Kaposi's sarcoma, glioblastoma, bladder cancer, head and neck cancer, glioma, colorectal cancer, genitourinary cancer and gastrointestinal cancer. In certain embodiments, the active agent is a chemotherapeutic drug. Chemotherapeutic drugs are well-known in the art and include alkylating agents such as cisplatin, anti-metabolites such as mercaptopurine, taxanes such as paclitaxel, topoisomerase inhibitors such as topotecan, and antitumor antibiotics such as doxorubicin. Anti-tumor active agents also include antibodies such as Herceptin. In particular embodiments, the active agent effective in the treatment of cancer is a protein (or nucleic acid encoding the same) selected from: a bispecific antibody that binds Pax-FKHR fusion protein or a tumor suppressor such as p53, pRb, PTEN, APC, and CD95, BRCA1, BRCA2, DNA repair enzymes, proapoptotic genes, p16$^{INK4a}$, WT1, NF1 (neurofibromin 1), NF2 (merlin or neurofibromin 2), TSC1 (hamartin), TSC2 (tuberin), DPC4, SMAD4, DCC, LKB1, STK11, MSH2, MLH1, CDH1 (E-cadherin), VHL, PTCH, (patched), MEN1, BLM, NBS1, MRE11A, ATM, hRad50, NER enzymes (such as XPA, XPB, XPC, XPD, DDB2, ERCC4, RAD2, and POLH), ERCC6, ERCC8, RECQL2, FANCA, FANCC, FANCD2, FANCE, FANCF, FANCG, FANCI, FANCJ, FANCL, FANCM, MLH1, MSH2, MSH6, PMS, and PMS2.

In certain embodiments the compositions and methods herein may be used to treat a disease or disorder involving dysfunction of nuclear receptors, and the conjugate is transported into cells in which altered nuclear receptor function is desired. In certain embodiments, the nuclear receptors are steroid, thyroid, retinoid, or orphan nuclear receptors. In certain embodiments, the orphan nuclear receptor is a SAR (selective androgen receptor), PPAR, PPARβ, PPAR, NUC1, FAAR, PPAR, RevErbA, EAR-1, RVR, RevErbAβ, BD73, HZF2, ROR, RZR, RORβ, RZRβ, ROR, TOR, LXR, RLD1, LXRβ, UR, NER, RIP15, OR1, FXR, RIP14, HRR1, PXR.1, PXR.2, SXR, ONR1, xOR6, BXR, hCAR1, MB67, mCAR1, HNF4, HNF4β, HNF4, RXR, RXRβ, H2RIIBP, RXR, TR2, TR2-11, xDOR2, aDOR1, TR4, TAK1, TR2R1, Tlx, TLL, xTLL, COUP-TFI, COUPTFA, EAR3, SVP44, COUP-TFII, COUPTFB ARP1, SVP40, xCOUP-TFIII, COUP-TF, SVP46, EAR2, ERR, ERR1, ERRβ, ERR2, ERR, NGFI-β, NUR77, N10, TR3, NAK1, TIS1, NURR1, NOT, RNR1, HZF-3, TINUR, TR3β, NOR-1, MINOR, TEC, CHN, FTZ-F1, SF1, ELP, AD4BP, FTF, LRH1, PHR1, CPF, FFLR, FF1rA, GCNF, RTR, DAX1, AHCH, or SHP. Depending on the disease to be treated, one of skill in the art will recognize whether the disease should be treated by increasing the levels of a nuclear receptor or decreasing the levels or activity of a nuclear receptor. Levels of the nuclear receptor may be increased, for example, by administering a nucleic acid encoding the nuclear receptor. Activity of the nuclear receptor may be decreased, by example, by administering an inhibitory antibody. Nuclear receptors, and the diseases caused by mutations in them, are as follows: Androgen receptor (CAIS/PAIS, complete/partial androgen insensitivity syndrome; Gynecomastia; interfility; SBMA; Kennedy's disease; Prostate Cancer; perineal hypospadias), DAX-1 (adrenal hypoplasia congenita, Adrenal insufficiency, delayed-onset, and hypogonadotropic hypogonadism), Vitamin 3D receptor (Vitamin D Resistant-rickets type IIA); HNF4 alpha (Maturity-onset diabetes of the young); Mineralocoricoid receptor (Pseudohypoaldosteronism, type 1; autosomal dominant; Hypertension, early-onset, autosomal dominant, with exacerbation in pregnancy), Thyroid hormone beta-1 (thyroid hormone resistance), Glucocorticoid receptor (Primary cortisol resistance familial Glucocorticoid resistance), PPAR gamma (Diabetes Mellitus, insulin-resistant, with acanthosis nigricans and hypertension; colon cancer; Inflammatory bowel disease), HNF4 alpha (Type II Diabetes), and ERa (Osteoporosis, Breast cancer). In particular embodiments, the active agent effective in the treatment of a nuclear receptor-mediated disorder is the protein deficient in the above-mentioned diseases, or a nucleic acid that up-regulates its expression. Those of the above diseases that are caused by inappropriately high expression of the mutant gene may be treated by administering a nucleic acid that down-regulates its expression.

In some aspects, a skeletal muscle disorder may be treated by altering the activity and/or levels of an orphan nuclear receptor. Orphan nuclear receptors and diseases associated with them are known in the art, for example in Smith et al., "Orphan Nuclear Receptors: therapeutic opportunities in skeletal muscle" Am J Physiol Cell Physiol 291:203-217, 2006. For example, dysfunction of LXR-α, LXR-β, farnesoid X receptor (FXR), PPAR-α, -β/δ, and -γ, liver receptor homolog-1, and the small heterodimeric partner can cause dyslipidemia, diabetes, obesity, inflammation, and cardiovascular disease. In addition, ERR-α, ROR-α, Rev-erb-α and -β, and Nur77 control several processes including lipid absorpotion, lipolysis, inflammation, and myokine expression. Specifically, PPAR-δ coordinates glucose tolerance, fatty acid oxidation, and energy expenditure in skeletal muscle as well as in adipose tissue. PPAR-α regulates fatty acid oxidation, and stimulates mitochondrial β-oxidation and thermogenesis in the muscles. In addition, LXR-α and -β regulate lipid metabolism in skeletal muscle. ERR-α, -β, and -γ are involved in ovesity, lipid metabolism, and oxidative phosphorylation, and mitochondrial respiration in skeletal and cardiac muscle. Also, ROR nuclear receptors (including ROR-α1, -α2, α3, and -αα) are involved in muscle dysfunction such as ataxia, as well as dyslipidemia, atherosclerosis, and hypersensitive inflammatory response. Rev-erbs (including Rev-erbα and Rev-erbβ) are also involved in dyslipidemia. In addition, the NR4A family (including Nurr1, Nur11, and NOR-1) is thought to be involved in obesity, energy balance, homeostasis, lipid utilization, and lipid and carbohydrate homeostasis. Based on the disclosures herein in combination with the state of the art, one of skill in the art will recognize which orphan nuclear receptor protein, orphan nuclear receptor-modulating nucleic acid, or orphan nuclear receptor agonist or antagonist, may be administered in conjunction with the methods and compositions herein, in order to effectively treat an orphan nuclear receptor-mediated disease.

In certain embodiments the compositions and methods herein may be used to treat a disease or disorder involving dysfunction of factors controlling chromatin modification, and the conjugate is transported into cells in which altered chromatin modification state is desired. In certain embodiments, the chromatin modification factors are histone deacetylases, histone methyltransferases, histone kinases, histone phosphatases, histone ubiquitinylating enzymes, or histone poly-ADP-ribosylases. Also, chromatin assembly factors and nucleosome remodeling factors (and nucleic acids modulating their expression) may be administered. In certain embodiments, DNA methyltransferases (such as DNMT1, DNMT2, DNMT3) or nucleic acids modulating their expression may be administered in order to treat diseases associated with altered DNA methyltransferase function, such as ICF Syndrome.

In certain embodiments, the disease or disorder involves incorrect hormone levels. The hormone levels may be inappropriately high or low. If the disease is associated with low hormone levels, one may administer a gene (or gene product) in the synthesis pathway for that hormone. For example, to treat low testosterone levels, a gene or gene product of 17β hydroxysteroid dehydrogenase, 3β hydroxysteroid dehydrogenase, or 17,20 lyase may be administered. Alternatively, if the disease is associated with elevated hormone levels, a nucleic acid (such as a siRNA) designed to reduce levels of the hormone synthesis pathway components may be administered. Hormones include testosterone, estrogen, estradiol, and progesterone.

In certain embodiments, the methods herein may be used to target therapeutic antibodies, or nucleic acids encoding them, to particular target cells. The antibodies may be, for example, monoclonal antibodies, polyclonal antibodies, single-chain antibodies, or bi-specific antibodies. Suitable therapeutic antibodies include, but are not limited to, Anti_EGFr antibodies (e.g., panitumamab, Erbitux (cetuximab), matuzumab, IMC-I IF 8, TheraCIM hR3), denosumab, Avastin (bevacizumab), Anti-HGF antibodies, Humira (adalimumab), Anti-Ang-2 antibodies, Herceptin (trastuzumab), Remicade (infliximab), Anti-CD20 antibodies, rituximab, Synagis (palivizumab), Mylotarg (gemtuzumab oxogamicin), Raptiva (efalizumab), Tysabri (natalizumab), Zenapax (dacliximab), NeutroSpec (Technetium ($^{99m}$Tc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

In certain embodiments, the therapeutic agent is a proteasome inhibitor. Proteasome inhibitors may be used, for example, in the treatment of infectious diseases like HIV/AIDS and Hepatitis C, and for cancer therapy. In certain embodiments, the protease inhibitor is an antibody that binds a protease.

In certain embodiments, the subject conjugates can be used to deliver an expression construct to cells, such as muscle cells, that encodes a therapeutic protein. For instance, the expression construct can encode a therapeutic protein that is secreted by the transduced cell. For example, the expression construct acid can encode an angiogenic growth factor such as VEGF, a fibroblast growth factor such as basic FGF or FGF-4, placental growth factor, hepatocyte growth factor, angiogenin, angiopoietin-1, pleiotrophin, transforming growth factor (α or β), or tumor necrosis factor α. The expression construct also can encode a natiuretic peptide such as an atrial natiuretic peptide (ANP) or a brain natriuretic peptide (BNP), prostacyclin synthase, nitric oxide synthase, angiostatin, endostatin, erythropoietin (EPO), blood factors (such as coagulation factors like Factor I, II, III, IV, V, VII, VIII, IV, X, XI, XII and XIII), GM-CSF, or an interleukin such as IL-1, 2, 3, 4, 5, 6, 7, 8, 9, 10, 11, 12, 13, 14, 15, 16, 17, or 18. The expression construct can encode an adhesion molecule such as a selectin (e.g., E, L, or P selectin), an extracellular matrix protein (e.g., collagen type I, III, or IV; fibronectin; laminin; or vitronectin), an integrin (e.g., $\alpha_5\beta_1$), or an intracellular adhesion molecule such as ICAM or a vascular cell adhesion molecule (VCAM).

In either case, the expression construct that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus. The inducer also can be an illumination agent such as light and light's various aspects, which include wavelength, intensity, fluorescence, direction, and duration.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the cell(s). Sufficient expression, however, may sometimes be obtained without such additional elements.

Vectors also can include other elements. For example, a vector can include a nucleic acid that encodes a signal peptide such that the encoded polypeptide is directed to a particular cellular location (e.g., a signal secretion sequence to cause the protein to be secreted by the cell) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Viral vectors can be used to form the conjugates, and include adenovirus, adeno-associated virus (AAV), retroviruses, lentiviruses, vaccinia virus, measles viruses, herpes viruses, and bovine papilloma virus vectors. See, Kay et al. (1997) Proc. Natl. Acad. Sci. USA 94:12744-12746 for a review of viral and non-viral vectors. Viral vectors are modified so the native tropism and pathogenicity of the virus has been altered or removed. The genome of a virus also can be modified to increase its infectivity and to accommodate packaging of the nucleic acid encoding the polypeptide of interest.

Non-viral vectors can also be used in the subject conjugates.

To further illustrate, in one embodiment, the mammalian serum protein that is encoded by the vector is selected from the group consisting of a tissue-type plasminogen activator, a receptor of a tissue-type plasminogen activator, a streptokinase, a staphylokinase, a urokinase, and coagulation factors. The invention also provides a method for treating associated with the formation of clots in its circulation, including the step of administering to the mammal a conjugate that causes the recombinant expression and secretion into the blood, such as from transduced muscle cells, of a therapeutically effective amount of such a mammalian serum protein.

In another embodiment, the mammalian serum protein is glucocerebrosidase. The invention also provides a method of treating a patient having Gaucher disease, including the step of administering to the patient a conjugate that causes the recombinant expression and secretion into the blood, such as from transduced muscle cells, of a therapeutically effective amount of glucocerebrosidase.

In still another embodiment, the mammalian serum protein is α-galactosidase A. The invention also provides a method of treating a mammal having Fabry disease, including the step of administering to the patient a conjugate that causes the recombinant expression and secretion into the blood, such as from transduced muscle cells, of a therapeutically effective amount of α-galactosidase A.

In still another embodiment, the mammalian serum protein is a cytokine. The cytokine can be selected from the group consisting of IFN-α, IFN-β, IFN-γ, IL-2, IL-3, IL-4, IL-5, IL-6, IL-7, IL-8, IL-9, IL-10, IL-12 and IL-15. The invention also provides a method of treating a mammal having cancer or a bacterial or viral infection, including the step of administering to the mammal a conjugate that causes the recombinant expression and secretion into the blood, such as from transduced muscle cells, of a therapeutically effective amount of such a cytokine.

In still another embodiment, the mammalian serum protein is a peptide hormone. The peptide hormone can be selected from the group consisting of antimullerian hormone (AMH), adiponectin, adrenocorticotropic hormone (ACTH), angiotensinogen and angiotensin, antidiuretic hormone (ADH), atrial-natriuretic peptide (ANP), calcitonin, cholecystokinin (CCK), corticotropin-releasing hormone (CRH), erythropoietin (EPO), follicle stimulating hormone (FSH), gastrin, glucagon, gonadotropin-releasing hormone (GnRH), growth hormone-releasing hormone (GHRH), human chorionic gonadotropin (hCG), growth hormone (GH), insulin, insulin-like growth factor (IGF), leptin, luteinizing hormone (LH), melanocyte stimulating hormone (MSH or α-MSH), neuropeptide Y, oxytocin, parathyroid hormone (PTH), prolactin (PRL), relaxin, renin, secretin, somatostatin, thrombopoietin, thyroid-stimulating hormone (TSH), and thyrotropin-releasing hormone (TRH). The invention also provides a method for hormone replacement therapy in a mammal, including the step of administering to the mammal a conjugate that causes the recombinant expression and secretion into the blood, such as from transduced muscle cells, of a therapeutically effective amount of such a peptide hormone.

In still other embodiments, the subject conjugate can be selected to include an expression vector that causes the recombinant expression and secretion into the blood, such as from transduced muscle cells, of an enzyme selected from the group consisting of L-asparagine, L-glutaminase-L-asparaginase, L-methioninase, L-phenylalanine, ammonia-lyase, L-arginase, L-tyrosinase, L-serine dehydratase, L-threonine deaminase, indolyl-3-alkane hydroxylase, neuraminidase, ribonuclease, a protease, pepsin, and a carboxypeptidase. Such constructs can be used as part of a treatment program for cancer.

In another embodiment, the subject conjugate can be selected to include an expression vector that causes the recombinant expression and secretion into the blood of lysostaphin. The invention also provides a method of treating a mammal having a bacterial infection, including the step of administering such a conjugate.

In certain embodiments, the subject methods and compositions are used to deliver a prodrug of any of the drugs listed herein.

Pharmaceutical compositions including a disclosed conjugate may be used in the methods described herein. Thus, in one embodiment, a pharmaceutical composition including a conjugate present in an amount effective to treat a disease or disorder affecting a tissue expressing a nucleoside transport pathway in a subject is used in methods described herein. In another embodiment, a pharmaceutical composition including a conjugate present in an amount effective to treat a disease or disorder of skeletal muscle in a subject is used in methods described herein. In addition to the conjugate, the pharmaceutical composition may also contain other therapeutic agents, and may be formulated, for example, by employing conventional vehicles or diluents, as well as pharmaceutical additives of a type appropriate to the mode of desired administration (for example, excipients, preservatives, etc.) according to techniques known in the art of pharmaceutical formulation.

In certain embodiments, the compositions disclosed herein are formulated with additional agents that promote entry into the desired cell or tissue. Such additional agents include micelles, liposomes, and dendrimers.

The term "effective amount" of an active agent refers an amount that is non-toxic to a subject or a majority or normal cells, but is an amount of the active agent that is sufficient to provide a desired effect (e.g., treatment of a skeletal muscle disorder, metabolic disorder, blood disorder, or cancer). This amount may vary from subject to subject, depending on the species, age, and physical condition of the subject, the severity of the disease that is being treated, the particular conjugate, or more specifically, the particular active agent used, its mode of administration, and the like. Therefore, it is difficult to generalize an exact "effective amount," yet, a suitable effective amount may be determined by one of ordinary skill in the art.

The term "pharmaceutically acceptable" refers to the fact that the carrier, diluent or excipient must be compatible with the other ingredients of the formulation and not deleterious to the recipient thereof. For example, the carrier, diluent, or excipient or composition thereof may be administered to a subject along with a conjugate of the invention without causing any undesirable biological effects or interacting in an undesirable manner with any of the other components of the pharmaceutical composition in which it is contained.

Pharmaceutical compositions including the conjugate may be administered by any suitable means, for example, parenterally, such as by subcutaneous, intravenous, intramuscular, intrathecal, or intracisternal injection or infusion techniques (e.g., as sterile injectable aqueous or non-aqueous solutions or suspensions) in dosage formulations containing non-toxic, pharmaceutically acceptable vehicles or diluents. In certain embodiments the conjugate is administered parenterally, or more preferably, intravenously.

The mode of delivery chosen for administration of conjugates according to the present invention to a subject, such as a human patient or mammalian animal, will depend in large part on the particular active agent present in the conjugate and the target cells. In general, the same dosages and administration routes used to administer the active agent alone will also be used as the starting point for the conjugate. However, it is preferred that smaller doses be used initially due to the expected increase in cellular penetration of the active agent. The actual final dosage for a given route of administration is easily determined by routine experimentation. In general the same procedures and protocols that have been previously used for other antibody-based targeting conjugates (e.g., parenterally, intravenous, intrathecal, and the like) are also suitable for the conjugates of the present invention.

The pharmaceutical compositions of the conjugate can be administered either alone or in combination with other therapeutic agents, may conveniently be presented in unit dose form and may be prepared by any of the methods well known in the art of pharmacy. All methods include bringing the conjugate into association with the carrier, which constitutes one or more accessory ingredients. In general, the pharmaceutical compositions are prepared by uniformly and intimately bringing the active ingredient into association with a liquid carrier. In a pharmaceutical composition, the conjugate is included in an amount sufficient to produce the desired effect upon the process or condition of disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, parenteral delivery, including intramuscular, subcutaneous, intramedullary, intrathecal, intraventricular, intravenous, or intraperitoneal. For injection, the pharmaceutical compositions of the invention may be formulated in aqueous solutions, preferably in physiologically compatible buffers such as Hanks' solution, Ringer's solution, or physiologically buffered saline.

The present disclosure also provides a pharmaceutical composition including a conjugate described herein and an agent that promotes ENT2 expression in a tissue. In some aspects, the agent that promotes ENT2 expression in a tissue is an agent that inhibits hypoxia or an agent that inhibits HIF-1. The tissue may be a hypoxic tissue, such as a hypoxic tumor, a tissue with insufficient vasculature, an ulcer, a diabetic ulcer, a poorly-healing wound, an ischemic area, an ischemic area resulting from stroke, or an ischemic area resulting from cardiovascular disease. In certain embodiments, the agent that inhibits HIF-1a is a siRNA, an RNAi construct, a hairpin RNA, or a miRNA that reduces HIF-1a exprsesion. In some embodiments, the HIF-1a inhibitor is a chemotherapeutic drug, topotecan, NSC 644221, PX-478, YC-1, 17-AAG, or bevacizumab. In certain embodiments, the agent that inhibits hypoxia is an agent that normalizes tumor vasculature, or an agent that alters the redox state of a tissue. The agent that inhibits hypoxia may be excess oxygen, TSC, or almitrine. Excess oxygen may be delivered, for example, by intubation, an oxygen mask, or a hyperbaric chamber. In certain embodiments, the agent that promotes ENT2 expression is an inhibitor of a gene that downregulates ENT2, such as HIF-1α. In other embodiments, the agent that promotes ENT2 expression is a nucleic acid encoding ENT2, for example an expression construct that drives expression of ENT2 or any fragment thereof having essentially the same therapeutic transport activity as full-length ENT2.

Furthermore, herein is provided a method of treating an ENT-2 deficient tissue, wherein the method includes: a) administering an agent that promotes ENT2 exprssion and/or activity, and b) administering one of the conjugates disclosed herein.

In certain aspects, a conjugate as described herein may be adminstered together with ATP or an ATP-generating agent. These agents may be used to inhibit hypoxia and/or ischemia In certain aspects, ATP is specifically delivered to the target tissue, for example, using liposomes. Methods of delivering ATP to ischemic tissue are known in the art, and are described in U.S. Pat. No. 7,056,529 and Verma D et al., "ATP-loaded Liposomes Effectively Protect Mechanical Functions of the Myocardium from Global Ischemia in an Isolated Rat Heart Model", J Control Release, 2005 Nov. 28; 108(2-3): 460-471.

In certain embodiments, a patient is treated with a hypoxia-inhibiting agent and a conjugate herein prior to surgery, as a prophylactic treatment for ischemia caused by surgery.

A number of drugs affect tumor vasculature. While the mechanism of such drugs is not fully understood, there appear to be three broad classes of vasculature-targeting agents. First, an agent may be anti-angiogenic. Such agents prevent the growth of new blood vessels, starving the tumor of blood and oxygen. Such agents make a tumor more hypoxic. Second, an agent may collapse pre-existing tumor vasculature, also increasing the hypoxia of the tumor. Third, vasculature-normalizing agents reduce the abnormalities of the tumor vasculature. For example, they may reduce the number of excess epithelial cells in the tumor vasculature. These agents improve blood flow to the tumor and reduce hypoxia. Paradoxically, vasculature-normalizing agents may be used to impede tumor growth, by allowing other therapeutic molecules (such as chemotherapeutic drugs) better access to the tumor.

Some therapies previously thought to be anti-angiogenic may instead produce vasculature normalization. For example, one may block vascular endothelial growth factor (VEGF) or its receptor (VEGFR2), causing apoptosis of endothelial cells. Consequently there is a decrease in blood vessel diameter, density and permeability. There is also a decrease in interstitial fluid pressure and, at least in some instances, elevated oxygen tension (reviewed in Jain R et al., Nature Medicine 7, 987-989 (2001)). Various other therapeutics also contribute to vasculature normalization, including STI571, C225, and Herceptin, which block PDGFR, HER1 and HER2 signaling, respectively.

Therapeutic antibodies may be used to normalize tumor vasculature. For example, a neutralizing antibody (A4.6.1) against VEGF/VPF is described in Yuan F et al. (Proc Natl Acad Sci USA. 1996 Dec. 10; 93(25):14765-70.) Permeabolization of the tumor vasculature was observed a few hours after injection and lasted about 5 days. Also, the (VEGFR)-2 neutralizing antibody DC 101 may be used to normalize tumor vasculature as described in Kadambi et al., (Cancer Res. 2001 Mar. 15; 61(6):2404-8). Humanized versions of these antibodies, and antibody variants such as single-chain antibodies, may be used in accordance with the methods disclosed herein.

The invention will now be described in greater detail by reference to the following non-limiting examples.

Example 1

The anti-DNA antibody fragment 3E10 Fv has received attention as a novel molecular delivery vehicle due to its penetration into living cells with specific nuclear localization, absence of toxicity, and successful delivery of therapeutic cargo proteins in vitro and in vivo. In the present study, the pathway that allows 3E10 Fv to cross cell membranes was elucidated. In particular, the present study demonstrates that 3E10 Fv penetrates cells through a nucleoside salvage transporter. The results showed that 3E10 Fv is unable to penetrate into cells deficient in the equilibrative nucleoside transporter, ENT2, and reconstitution of ENT2 into ENT2-deficient cells restores 3E10 Fv transport into cell nuclei. These results represented the first demonstration of protein transport through a nucleoside salvage pathway.

Cell Lines

COS-7, K562, and CEM/ENT1 cells were purchased from the American Type Culture Collection (Rockville, Md.). A nucleoside transport-deficient porcine kidney tubular epithelial cells (PKNTD) were generated and transfected with plasmids containing nucleic acid encoding hENT1 or hENT2 to form PKNTD/ENT1 and PKNTD/ENT2 cells, respectively, as previously described (Ward et al., J. Biol. Chem. 275:8375-81, 2000).

Plasmids

A construct for expression of 3E10 Fv in the X-33 strain of *Pichia pastoris*, pPICZαA-Fv, was generated by ligating cDNA encoding the single-chain Fv fragment of mAb 3E10 into pPICZaA, as previously described (Weisbart et al., Cancer Lett. 195:211-9, 2003; and Weisbart et al., Int J Oncol 2004; 25:1113-8).

Purification of 3E10 Fv. 3E10 Fv was purified from the supernatant of *P. pastoris* transfected with pPICZaA-Fv as previously described (Weisbart et al., Cancer Lett. 195:211-9, 2003).

Cellular Penetration Assays

Purified 3E10 Fv was exchange-dialyzed into PBS prior to application to cells. After dialysis, 10% fetal calf serum was added to the buffer containing the 3E10 Fv. Control buffer was PBS with 10% fetal calf serum. For adherent cell lines (COS-7, PKNTD/ENT1, and PKNTD/ENT2), 50 μL of control buffer or 3E10 Fv in PBS+10% fetal calf serum was added to cells on 96-well plates for one hour. After incubation with 3E10 Fv, the antibody fragment was removed and cells were washed, fixed in chilled 100% ethanol, and stained with the 9E10 α-myc antibody as previously described (Weisbart et al., Cancer Lett. 195:211-9, 2003). For non-adherent cells (K562 and CEM/ENT1) cell pellets composed of ~200,000 cells were re-suspended in 100 μL control buffer or 10 μM 3E10 Fv and allowed to incubate with intermittent shaking at 37° C. for one hour. Cells were then centrifuged at 100 g for 2 minutes and washed three times with PBS. Next, cells were spread on glass slides and allowed to dry overnight. Cells were then fixed in chilled 100% ethanol for ten minutes, washed three times in PBS, and stained with the 9E10 α-myc antibody.

Nucleoside Transporter Inhibition Assay

Nitrobenzylmercaptopurine riboside (NBMPR) was purchased from Sigma (St. Louis, Mo.), and a stock solution of 100 mM NBMPR in DMSO was prepared. To control for the effects of DMSO in cell culture, DMSO was added to control buffers not containing NBMPR. The concentration of DMSO in all control and experimental buffers was 0.1%. COS-7 cells were pre-treated for 30 minutes with control buffer (PBS+10% fetal calf serum) or buffer containing 10 μM or 100 μM NBMPR. Buffers were then replaced with control buffer or 10 μM 3E10 Fv in the presence or absence of 10 μM or 100 μM NBMPR for one hour. Cells were then washed, fixed, and stained with the 9E10 α-myc antibody.

Microscopic Images

Images of cells were acquired with an Olympus IX70 inverted microscope with RC reflected light fluorescent attachment and MagnaFire SP Digital Imaging System (Olympus, Melville, N.Y.) as described previously (Weisbart et al., J Immunol 164:6020-6, 2000). Scale bar in cell images=5 μm.

The single chain Fv fragment of the 3E10 anti-DNA autoantibody (3E10 Fv) has recently been harnessed as a novel molecular delivery vehicle due to its specific nuclear localization and apparent lack of toxicity (Weisbart et al., J. Autoimmun. 11(5), 539-46, 1998). 3E10 Fv and Fv-fusion proteins readily transduce across cell membranes and penetrate into cell nuclei, and 3E10 Fv has successfully delivered biologically active proteins such as Hsp70 (Hansen et al., Brain Res. 1088(1), 187-96, 2006) and p53 (Weisbart et al., Int. J. Oncol. 25(6), 1867-1873, 2004) into living cells in vitro. Moreover, 3E10 Fv mediated full-length p53 protein therapy in vivo (Hansen et al., Cancer Res. 67(4), 1769-74, 2007). The pathway that carries 3E10 Fv across cell membranes and into cell nuclei, however, has not been identified previously.

Previous studies implicated DNA binding as important in 3E10 Fv transduction into cell nuclei. Specifically, mutations that abrogate DNA binding by the antibody render it incapable of cellular penetration (Zack et al., *J. Immunol.* 157(5), 2082-8, 1996). The association between cellular penetration and DNA binding distinguished 3E10 Fv from other protein transduction domains and suggested the potential involvement of nucleoside salvage pathways in 3E10 Fv transport. Both concentrative (CNT) and equilibrative (ENT) nucleoside transporters mediate the uptake of nucleosides and nucleobases by mammalian cells (Kong et al., *Curr. Drug Metab.* 5(1):63-84, 2004). Other studies demonstrating 3E10 Fv penetration into COS-7 cells that lack endogenous CNTs, suggested that CNTs do not play a major role in 3E10 Fv transport (Hansen et al., *Brain Res.* 1088(1), 187-96, 2006; and Toan et al., *Pflugers Arch.* 447(2), 195-204, 2003). Thus, the role of ENTs in 3E10 Fv transport was examined in the present study.

ENT1 and ENT2, which each mediate equilibrative nucleoside transport in mammalian cells, are inhibited by high concentrations of NBMPR (Ward et al., *J. Biol. Chem.* 275(12):8375-81, 2000). NBMPR was tested for inhibition of 3E10 Fv transport. Purified 3E10 Fv (constructed with His$_6$ tag for purification and myc tag for identification) migrated as a single ~30 kDa protein on SDS-PAGE. Transduction of 3E10 Fv into COS-7 cells was confirmed by incubating cells with 10 μM 3E10 Fv for one hour at 37° C., followed by Western blot analysis of cell lysates or immunocytochemical staining of cells. Western blot analysis of cell lysates demonstrated the presence of a ~30 kDa myc-tagged protein inside cells treated with 3E10 Fv, which indicated penetration of the full-length antibody fragment. Furthermore, immunocytochemical staining confirmed nuclear localization by 3E10 Fv, consistent with previous confocal microscopy and immunocytochemical studies on the antibody (Hansen et al., Brain Res. 1088(1), 187-96, 2006; and Weisbart et al., J. Immunol. 164(11), 6020-6, 2000). Next, COS-7 cells were pre-treated for 30 minutes with control buffer or buffer containing 100 μM NBMPR prior to a one hour incubation with 10 μM 3E10 Fv in the presence or absence of NBMPR. Subsequent immunocytochemical staining of the cells demonstrated that 100 μM NBMPR suppressed nuclear penetration by 3E10 Fv, which suggested that ENT1 or ENT2 is involved in 3E10 Fv transport.

To resolve which of the ENTs was linked to 3E10 Fv transport, 3E10 Fv penetration into COS-7 cell nuclei was tested in the presence of a lower dose of NBMPR to take advantage of the different $K_i$ of NBMPR for ENT1 and ENT2 (0.4 nM versus 2.8 µM, respectively) (Ward et al., *J. Biol. Chem.* 275(12):8375-81, 2000). Thus, at 10 µM NBMPR ENT1 activity is completely inhibited while ENT2 retains moderate activity. In contrast to the distinct inhibition of 3E10 Fv transport provided by 100 µM NBMPR, 3E10 Fv successfully penetrated COS-7 cell nuclei in the presence of 10 µM NBMPR. This result suggested that ENT2, not ENT1, mediated transport of 3E10 Fv. The decreased nuclear staining intensity in cells treated with 3E10 Fv+10 µM NBMPR compared to cells treated with 3E10 Fv alone likely reflects partial inhibition of 3E10 Fv transport due to the expected >50% suppression of ENT2 activity by 10 µM NBMPR.

As an additional approach to identifying the equilibrative nucleoside transporter(s) involved in 3E10 Fv transduction, 3E10 Fv transduction into the CEM/ENT1 cell line that expresses ENT1 but lacks ENT2 (Crawford et al., *J. Biol. Chem.* 273(9), 5288-93, 1998) was examined. K562 leukemia cells, which express both ENT1 and ENT2 (Huang et al., *Nucleosides Nucleotides Nucleic Acids* 23(8-9), 1445-50, 2004), were used as a positive control. CEM/ENT1 cells (which express ENT1 but not ENT2) and K562 cells were incubated with control buffer or 10 µM 3E10 Fv for one hour. Cells were then washed, fixed, and stained with the α-myc antibody. Control K562 cells and CEM/ENT1 cells showed no staining Consistent with the studies in COS-7 cells, immunocytochemical staining of the 3E10 Fv-treated K562 cells demonstrated penetration of the antibody fragment into ~100% of the cells. CEM/ENT1 cells treated with 3E10 Fv, however, showed no staining. This result demonstrated that absence of ENT2 significantly impaired transduction by 3E10 Fv into cells. Taken together, the inhibition of 3E10 Fv transport by high concentrations of NBMPR and failure of 3E10 Fv to penetrate a cell line lacking ENT2 strongly support a role of ENT2 in 3E10 Fv transport.

To verify that ENT2 facilitates 3E10 Fv intranuclear protein transduction, experiments were performed on nucleoside transporter-deficient PK15 cells (PKNTD) with either ENT1 or ENT2 reconstituted through stable transfection and expression of ENT1 or ENT2 cDNA (Ward et al., *J. Biol. Chem.* 275(12):8375-81, 2000). PKNTD/ENT1 and PKNTD/ENT2 cells were treated with control buffer (i.e., control cells) or 10 µM 3E10 Fv for one hour. Cells were then washed, fixed, and stained with the α-myc antibody. Control PKNTD/ENT1 and PKNTD/ENT2 cells showed an absence of staining. Similarly, PKNTD/ENT1 cells treated for one hour with 10 µM 3E10 Fv showed an absence of staining, exhibiting no evidence of nuclear penetration, which indicated a failure of the antibody fragment to penetrate the ENT2-deficient cells. This result was consistent with the results obtained with the CEM/ENT1 cells. In contrast, 3E10 Fv-treated PKNTD/ENT2 cells exhibited distinct nuclear staining, which indicated that restoration of ENT2 to the nucleoside transporter deficient cells significantly augmented nuclear penetration by 3E10 Fv. This result confirmed that the presence of ENT2 facilitates nuclear penetration by 3E10 Fv and verified protein transduction of the antibody fragment through the ENT2-mediated nucleoside salvage pathway.

The nucleoside salvage pathways have been studied in detail, but protein transport through or related to nucleoside salvage has not been previously described. While not wishing to be bound by any particular theory, 3E10 Fv may be carried into cells by virtue of its binding to nucleosides or nucleobases that are subsequently transported into cells by ENT2. Alternatively, 3E10 Fv may mimic the structure of a nucleoside or nucleobase that is recognized and transported into cells by ENT2. Elucidation of the specific mechanism by which ENT2 facilitates 3E10 Fv transport should yield further insights into both protein transduction and nucleoside salvage pathways. Furthermore, since ENT2 is located in both plasma and nuclear membranes, it will be important to ascertain whether ENT2 facilitates transport of 3E10 Fv across both cellular and nuclear membranes or if another pathway is involved in nuclear penetration (Mani et al., *J. Biol. Chem.* 273(46), 30818-325, 1998).

With regard to molecular therapy, the linkage between ENT2 and nuclear penetration by 3E10 Fv reported herein further establishes 3E10 Fv as a novel molecular delivery vehicle that is distinct from other protein transduction domains previously described. Endosomal localization by cell-penetrating peptides limits their role in molecular therapy (Jones et al., *Br. J. Pharmacol.* 145(8), 1093-102, 2005; and Kaplan et al., *J. Control Release* 102(1):247-53, 2005), but the identification of 3E10 Fv transport through ENT2 provides a rationale for future studies on the use of 3E10 Fv in delivering molecules such as siRNAs, antisense oligonucleotides, and transcription factors to cell nuclei.

Moreover, it is possible that toxic cell-penetrating antibodies utilize a nucleoside salvage pathway in cellular penetration. Thus, inhibition of nucleoside transporters may be a means of limiting tissue damage by cytotoxic autoantibodies in certain autoimmune diseases. The discovery of intranuclear protein transduction by 3E10 Fv through the ENT2-mediated nucleoside salvage pathway has profound implications for cell biology, pharmacology, and medicine.

Although the invention has been described with reference to the above example, it will be understood that modifications and variations are encompassed within the spirit and scope of the invention. Accordingly, the invention is limited only by the following claims.

What is claimed is:

1. A method of contacting an equilibrative nucleoside transporter (ENT)-2 conjugate to hypoxic tissue, comprising: (a) administering a cDNA encoding hENT2 or any fragment thereof having the same therapeutic transport activity as full-length hENT2, and (b) administering a conjugate, wherein the conjugate comprises: an antibody that is capable of being transported by an ENT2, and an active agent linked to the antibody, wherein the conjugate is transported by ENT2, wherein the antibody has the same binding specificity of an antibody as produced by the hybridoma having ATCC accession number PTA 2439.

2. The method according to claim 1, wherein the antibody is an antibody or an antigen binding fragment thereof.

3. The method according to claim 1, wherein the antibody or fragment thereof binds nucleic acid.

4. The method according to claim 1, wherein the agent is selected from the group consisting of hamartin (TSC1), tuberin (TSC2), or almitrine.

5. The method according to claim 1, wherein the agent is selected from the group consisting of topotecan, NSC 644221, PX-478, YC-1, 17-AAG, or bevacizumab.

* * * * *